United States Patent
Zheng et al.

(10) Patent No.: US 10,280,158 B2
(45) Date of Patent: May 7, 2019

(54) IMMUNE ADJUSTMENT COMPOUND, USE THEREOF AND PHARMACEUTICAL COMPOSITION COMPRISING SAME

(71) Applicant: SUZHOU CONNECT BIOPHARMACEUTICALS, LTD., Taicang, Jiangsu (CN)

(72) Inventors: Wei Zheng, San Diego, CA (US); Wubin Pan, Richmond (CA); Xin Yang, Taicang (CN)

(73) Assignee: SUZHOU CONNECT BIOPHARMACEUTICALS, LTD., Jiangsu (CN)

( * ) Notice: Subject to any disclaimer, the term of this patent is extended or adjusted under 35 U.S.C. 154(b) by 41 days.

(21) Appl. No.: 15/023,246

(22) PCT Filed: Sep. 15, 2014

(86) PCT No.: PCT/CN2014/086538
§ 371 (c)(1),
(2) Date: Aug. 3, 2016

(87) PCT Pub. No.: WO2015/039587
PCT Pub. Date: Mar. 26, 2015

(65) Prior Publication Data
US 2016/0347745 A1 Dec. 1, 2016

(30) Foreign Application Priority Data

Sep. 22, 2013 (CN) ............ 2013 1 0433018

(51) Int. Cl.
*C07D 413/10* (2006.01)
(52) U.S. Cl.
CPC .................. *C07D 413/10* (2013.01)
(58) Field of Classification Search
CPC ................................................ C07D 413/10
See application file for complete search history.

(56) References Cited

FOREIGN PATENT DOCUMENTS

| CN | 103450171 A | 12/2013 |
| WO | WO 03/105771 A2 | 12/2003 |
| WO | WO 2004/035538 A1 | 4/2004 |

OTHER PUBLICATIONS

English Translation of CN 103450171 A (43 pages).
International Search Report dated Dec. 17, 2014 for Application No. PCT/CN2014/086538, with English Translation (6 pages).
Australian Office Action titled "Examination report No. 1 for your standard patent application", for Australian Application No. 2014323822, dated Nov. 21, 2017, 4 Pages.

*Primary Examiner* — Joseph R Kosack
(74) *Attorney, Agent, or Firm* — Lewis Roca Rothgerber Christie LLP

(57) ABSTRACT

The present invention provides a compound represented by formula I, wherein R is a halogen element or a C1-C6 alkyl group. The compound has S1P1 receptor agonist activity and selective specificity and has obviously-shortened half-life in-vivo, and therefore the compound is a high-quality second-generation S1P1 receptor agonist. The present invention also provides a use of the compound in preparing medicine for treating diseases or symptoms mediated by an S1P1 receptor, a pharmaceutical composition comprising the compound, and uses of the compound and the pharmaceutical composition in treating diseases or symptoms mediated by the S1P1 receptor.

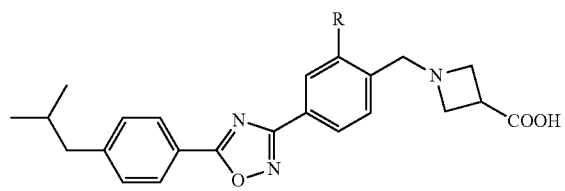

25 Claims, 5 Drawing Sheets

IMMUNE ADJUSTMENT COMPOUND, USE THEREOF AND PHARMACEUTICAL COMPOSITION COMPRISING SAME

CROSS-REFERENCE TO RELATED APPLICATION(S)

This application is a National Phase Patent Application and claims priority to and the benefit of International Application Number PCT/CN2014/086538, filed on Sep. 15, 2014, which claims priority to and the benefit of Chinese Patent Application Number 201310433018.6, filed Sep. 22, 2013, the entire contents of all of which are incorporated herein by reference.

TECHNICAL FIELD

The present invention relates to the field of medicine. Particularly, the present invention relates to a novel compound having an activity of S1P1 receptor agonists, a pharmaceutical composition comprising the compound, use of the compound and pharmaceutical composition for manufacturing a medicament for the treatment of disease mediated by S1P1 receptor and use of the compound and pharmaceutical composition for treating related disease mediated by S1P1 receptor.

BACKGROUND OF THE INVENTION

It is well known in the art that the presence of sphingosine-1-phosphate receptor-1 (S1P1) is required for the transport of lymphocytes from lymphatic tissues into the peripheral circulation. However, internalization of S1P1 may prevent lymphocytes from exiting lymphatic tissues, and thus those important immunocytes will be confined in lymphatic tissues.

Many studies suggested that there exist multiple S1P1 agonists which can bind to homologous receptors expressed on lymphocytes and result in the internalization of S1P1, thereby preventing the transport of lymphocytes. S1P1 receptor agonists can reduce the ability of human to initiate immune response by preventing the transport of lymphocytes, therefore they could serve as immunosuppressants for the treatment of various autoimmune diseases.

Many S1P1 agonists have been described and the most typical compound among them is FTY720 (also known as "Fingolimod"). Now, FTY720 is promoted and sold by Novartis under a trade name "Gilenya", for the treatment of Multiple sclerosis. Although FTY720 has clinical efficacy, it is a non-selective S1P receptor agonist and may activate several S1P receptors, such as S1P1, S1P2, S1P3, S1P4, and S1P5. The binding of FTY720 to S1P3 may result in a series of side effects, for example, bradycardia and tissue fibrosis. Therefore, many pharmaceutical companies and biotechnology groups are searching for the second generation of S1P1 agonist which is more specific and safer, so as to overcome the side effects of FTY720.

In addition to improving target specificity, shortening the in vivo half-life of drug (i.e. S1P1 receptor agonist) is another important object of screening the second generation of S1P1 agonist (Pan et al., 2013, ACS Medicinal Chemistry Letters, 4, p333). Traditionally, small molecule drugs with longer half-life are considered to be desirable, since a long half-life can avoid frequent administration of the drug. However, a long half-life may become a severe disadvantage for immunosuppressant drugs because the immunosuppressant drug may persistently inhibit the transport of lymphocytes, and thus decrease the number of lymphocytes in the peripheral blood, resulting in a reduced immune functioning and an increased risk of viral infections for drug users. The disadvantage above exists with S1P1 receptor agonist, such as FTY720, clinically used at present. In case of infection, it is often required to discontinue administration, in order to get lymphocytes in the peripheral blood return to a normal level as soon as feasible and restore the immune function of human body rapidly. As the half-life of FTY720 in the body is 6 to 9 days, a long time is needed for lymphocytes to revert to normal even after patients stop taking the medicine (Budde et al., 2002, Journal of the American Society of Nephrology, 13:1073-83).

Therefore, there is still a need for a novel S1P1 receptor agonist with high selectivity for S1P1 and a shorter half-life, to overcome deficiencies of the existing therapies.

SUMMARY OF THE INVENTION

In order to solve the technical problems above, the inventors carried out pharmaceutical chemical synthesis, and screened a large number of synthesized compounds through pharmacokinetic studies in rats in combination with studies on immune cell regulation and the like. It was found during the studies that novel compounds can be obtained by addition of halogen or alkyl to position 2 in compound as shown in Formula IA, which has been described as 1-{4-[5-(4-isobutylphenyl)-1,2,4-oxadiazol-3-yl]-benzyl}-3-azetidine carboxylic acid (Li et al., 2005, Journal of Medicinal Chemistry, 48 (20) 6169-6173; also known as "Compound 1" herein). Those compounds retained the potency of immune regulation in vitro and in vivo after intravenous and oral administration, and additionally the obtained compounds through substitution by halogen also have obviously reduced half-life after being administered in the two different ways.

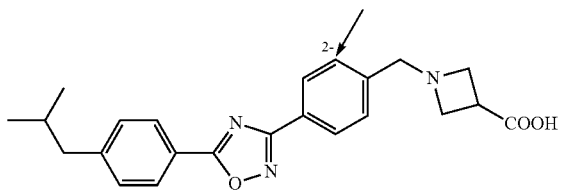

Formula IA (Compound 1)

Therefore, one purpose of the present invention is to provide a novel compound, to solve the deficiency in selectivity and half-life of existing S1P1 receptor agonists. Another purpose of the present invention is to provide a use of the compound for manufacturing a medicament. Yet another purpose of the present invention is to provide a pharmaceutical composition comprising the compound as major active ingredient. Still another purpose of the present invention is to provide a method for treating disease using the compound or the pharmaceutical composition. Still yet another purpose of the present invention is to provide a synthesis method of the compound.

In order to realize the above purposes, technical solutions provided by the present invention are as follows:

In one aspect, the present invention provides a compound as shown in Formula I,

Formula I

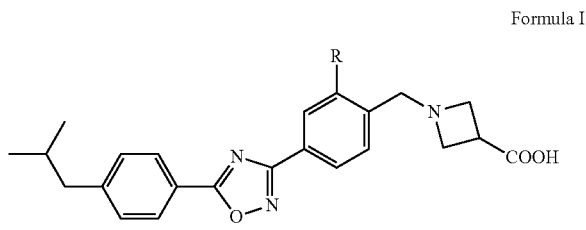

wherein, R is halogen or $C_1$-$C_6$ alkyl.

Preferably, R is F, Cl or Br; or R is C1-C3 alkyl, more preferably methyl.

The compound is, when R is F, 1-{2-fluoro-4-[5-(4-isobutylphenyl)-1,2,4-oxadiazol-3-yl]-benzyl}-3-azetidine carboxylic acid (also known as "Compound 2" herein), which is represented by Formula IB:

Formula IB (Compound 2)

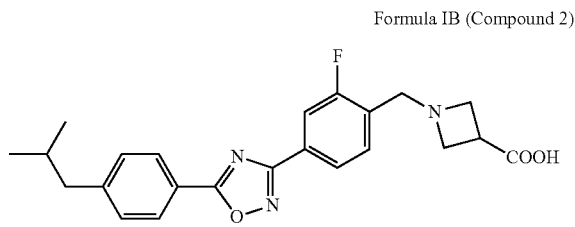 [SMILES: CC(C)Cc1ccc(-c2nc(-c3ccc(CN4CC(C(=O)O)C4)c(F)c3)no2)cc1]

The compound is, when R is Cl, 1-{2-chloro-4-[5-(4-isobutylphenyl)-1,2,4-oxadiazol-3-yl]-benzyl}-3-azetidine carboxylic acid (also known as "Compound 3" herein), which is represented by Formula IC:

Formula IC (Compound 3)

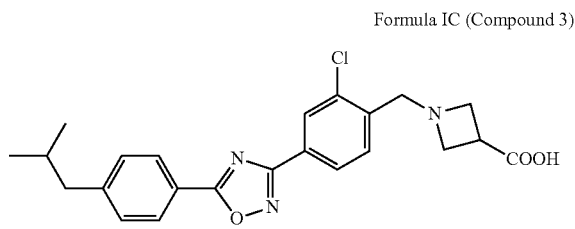 [SMILES: CC(C)Cc1ccc(-c2nc(-c3ccc(CN4CC(C(=O)O)C4)c(Cl)c3)no2)cc1]

The compound is, when R is Br, 1-{2-bromo-4-[5-(4-isobutylphenyl)-1,2,4-oxadiazol-3-yl]-benzyl}-3-azetidine carboxylic acid (also known as "Compound 4" herein), which is represented by Formula ID:

Formula ID (Compound 4)

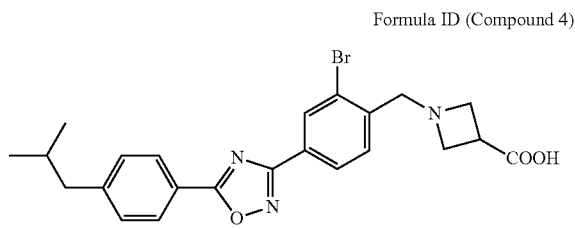 [SMILES: CC(C)Cc1ccc(-c2nc(-c3ccc(CN4CC(C(=O)O)C4)c(Br)c3)no2)cc1]

The compound is, when R is methyl, 1-{2-methyl-4-[5-(4-isobutylphenyl)-1,2,4-oxadiazol-3-yl]-benzyl}-3-azetidine carboxylic acid (also known as "Compound 5" herein), which is represented by Formula IE:

Formula IE (Compound 5)

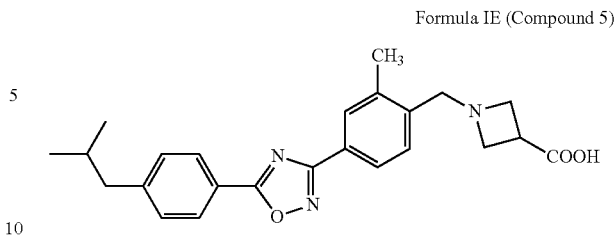

A large number of experiments showed that the compounds provided by the present invention had S1P1 agonistic activity, which was confirmed by the detected internalization of S1P1 and the reduced number of lymphocytes in the peripheral blood induced by the compounds. Meanwhile, the compounds provided by the present invention also had selective specificity for S1P1; especially the compounds did not induce cells expressing S1P3 subtype to internalize. Further, pharmacokinetic experiments of the compounds provided by the present invention showed that, the half-life of certain compounds was shortened significantly compared to that of compound represented by Formula IA, and was much shorter than that of FTY720.

Therefore, in another aspect, the present invention provides a use of above compounds for manufacturing a medicament for the treatment of disease or condition mediated by S1P1. Particularly, said disease or condition is selected from the group consisting of rheumatoid arthritis, multiple sclerosis, inflammatory enteritis, autoimmune disease, chronic inflammatory disease, asthma, inflammatory neuropathies, arthritis, transplantation, Crohn's disease, ulcerative colitis, lupus erythematosus, psoriasis, ischemia-reperfusion injury, solid tumor, disease associated with angiogenesis, disease of blood vessel, pain, acute viral disease, inflammatory bowel disease, insulin and non-insulin dependent diabetes mellitus, and other related immune diseases. Preferably, said disease or condition is selected from the group consisting of multiple sclerosis, rheumatoid arthritis, inflammatory enteritis and psoriasis.

As used herein, expression "treating" or "treatment" also refers to preventing above diseases or conditions or delaying symptoms and the like, apart from curing diseases or conditions mediated by S1P1.

In yet another aspect, the present invention provides a pharmaceutical composition comprising the compound provided by the present invention and optionally a pharmaceutically acceptable carrier. The pharmaceutical composition can be a medicinal formulation itself, or can be prepared as a medicinal formulation or a combined medicinal formulation with other excipient(s) or drug(s).

Specifically, the pharmaceutical composition provided by the present invention may be in a form of tablet, suppository, dispersible tablet, enteric-coated tablet, chewable tablet, orally disintegrating tablet, capsule, sugar-coated agent, granule, dry powder, oral solution, small needle for injection, lyophilized powder or large volume parenteral solution for injection; wherein, the pharmaceutically acceptable excipient may be selected from the group consisting of diluents, solubilizers, disintegrating agents, suspending agents, lubricants, binders, fillers, flavoring agents, sweeteners, antioxidants, surfactants, preservatives, wrapping agents and pigments, etc.

In still another aspect, the present invention provides a method for treating disease or condition mediated by S1P1, comprising administering to a subject a therapeutically effective amount of the compound or the pharmaceutical composition of the present invention. Preferably, said subject is a mammalian.

Wherein, said disease or condition is selected from the group consisting of rheumatoid arthritis, multiple sclerosis, inflammatory enteritis, autoimmune disease, chronic inflammatory disease, asthma, inflammatory neuropathies, arthritis, transplantation, Crohn's disease, ulcerativecolitis, lupus erythematosus, psoriasis, ischemia-reperfusion injury, solid tumor, disease associated with angiogenesis, disease of blood vessel, pain, acute viral disease, inflammatory bowel disease, insulin and non-insulin dependent diabetes mellitus, and other related immune diseases. Preferably, said disease or condition is selected from the group consisting of multiple sclerosis, rheumatoid arthritis, inflammatory enteritis and psoriasis.

The compound or pharmaceutical composition provided by the present invention can be co-administered with other therapies or therapeutic agents. What's more, doses of the compound or pharmaceutical composition needed for playing the role of treatment, prevention or delay depend on the particular compound to be administered, patient, specific disease or disorder and severity thereof, route and frequency of administration and so on, and need to be determined by the attending doctor in accordance with specific conditions.

In summary, the present invention provides a novel compound having an activity of S1P1 agonists, and the compound is obtained by substituting at position 2 in the compound represented by Formula IA with halogen, especially fluorine, chlorine or bromine or lower alkyl. It can be proven that the compounds of the present invention have the activity of S1P1 agonists by the experimentally detected internalization of S1P1 and the reduced number of lymphocytes in the peripheral blood. In addition, internalization induction experiments using cells expressing S1P3 subtype also prove that the compounds have a selective specificity for S1P1.

In particular, compared with known S1P1 agonists and the compound as shown in formula IA, the compounds of the present invention obtained through substitution with halogen have significantly shortened half-life. Pharmacokinetic experiments proven that the half-life of those compounds was shortened significantly from about 11 hours to less than 5.5 hours. Both intravenous and oral administration modes showed a significantly shortened half-life, which was consistent with the reduced parameter of mean residence time. What's more, it is inventive to substitute with specific substituents at specific positions. Moreover, although the half-life of the compound obtained by substituting at the same position with a lower alkyl, especially with methyl (Compound 5), is not shortened, the effects on lymphocytes in vivo are similar to those of compounds substituted with halogen. These results indicate that the compounds provided by the present invention are potential qualified second generation of S1P1 agonist.

In still yet another aspect, as for the compound represented by Formula IB (Compound 2), the present invention further provides a synthesis method which involves simple reaction conditions, and is convenient to post-treatment and suitable for industrialized manufacture with a high yield and stable process.

In short, the synthesis scheme of the present invention is as follows:

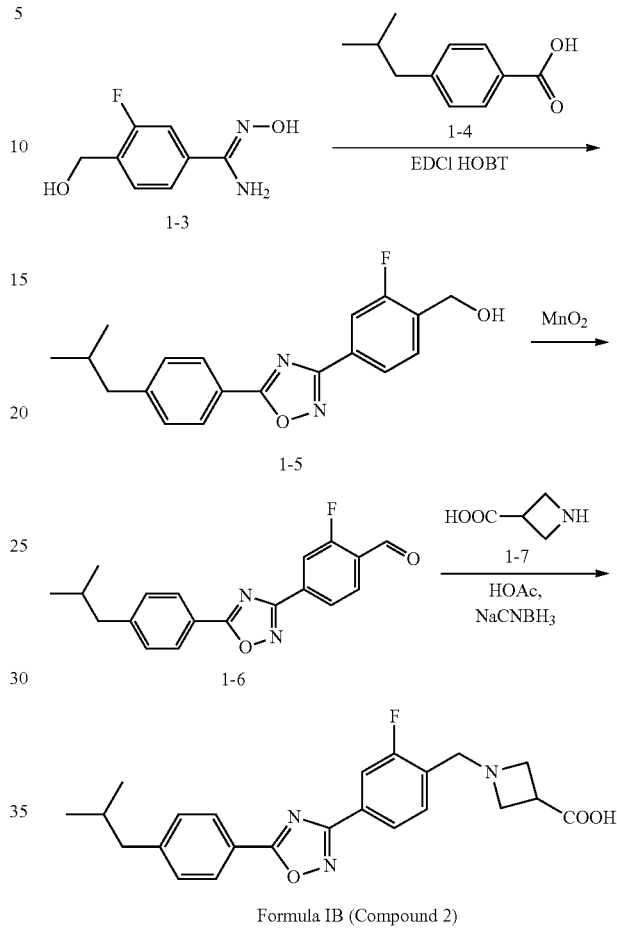

Formula IB (Compound 2)

Specifically, the present invention provides a synthesis method of 1-{2-fluoro-4-[5-(4-isobutylphenyl)-1,2,4-oxadiazol-3-yl]-benzyl}-3-azetidine carboxylic acid (also known as "Compound 2") as shown in Formula IB, comprising the following steps:

(1) reacting 3-fluoro-N'-hydroxy-4-hydroxymethyl benzamidine as shown in formula 1-3 with 4-isobutylbenzoicacid as shown in formula 1-4 in the presence of condensation agents 1-(3-dimethylaminopropyl)-3-ethylcarbodiimide hydrochloride and 1-hydroxybenzotrizole to generate the 2-fluoro-4-[5-(4-isobutylphenyl)-1,2,4-oxadiazol-3-yl]-benzyl alcohol as shown in formula 1-5:

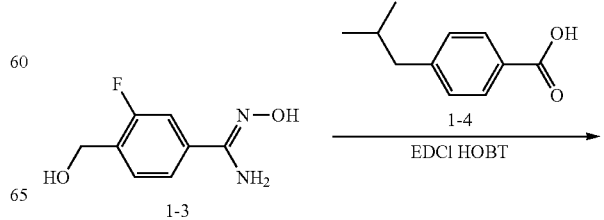

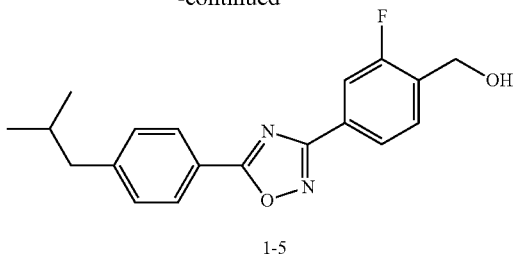

(2) reacting the 2-fluoro-4-[5-(4-isobutylphenyl)-1,2,4-oxadiazol-3-yl]-benzyl alcohol of formula 1-5 obtained in step (1) with manganese dioxide to generate 2-fluoro-4-[5-(4-isobutylphenyl)-1,2,4-oxadiazol-3-yl]-benzaldehyde as shown in formula 1-6:

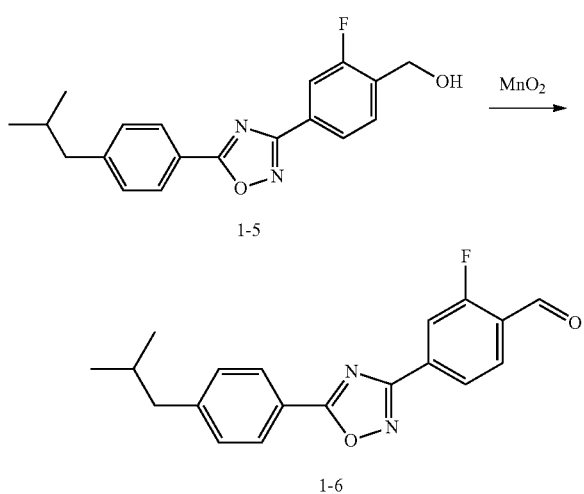

(3) reacting the 2-fluoro-4-[5-(4-isobutylphenyl)-1,2,4-oxadiazol-3-yl]-benzaldehyde as shown in formula 1-6 obtained in step (2) with azetidine-3-carboxylic acid as shown in formula 1-7 by using acetic acid as catalyst and sodium cyanoborohydride as reducing agent to generate the compound as shown in formula IB:

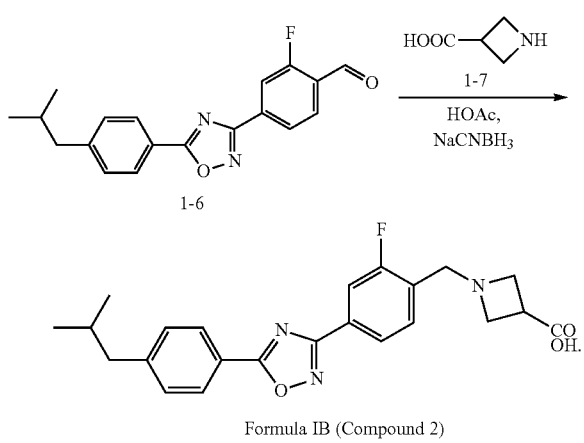

Formula IB (Compound 2)

According to preferred embodiments of the present invention, step (1) also comprises a step of purifying the obtained crude product after the generation of 2-fluoro-4-[5-(4-isobutylphenyl)-1,2,4-oxadiazol-3-yl]-benzyl alcohol as shown in formula 1-5; preferably, the purification is conducted through column chromatography or crystallization.

When conducting purification through crystallization, the crystallization solvent utilized is one or more selected from methanol, ethanol, acetone, dichloromethane, ethyl acetate, and water; preferably, the crystallization solvent is a mixture of methanol and water; more preferably, the crystallization solvent is a mixture of methanol and water in a ratio of 3:1 by volume. Preferably, the ratio of the crude product (in g, by weight) to the crystallization solvent (in ml, by volume) is 1:3-20, more preferably 1:5. Preferably, the crystallization is carried out at 20° C.

According to preferred embodiments of the present invention, the reaction of step (1) is carried out in a reaction solvent which is one or more selected from acetonitrile, N-methylpyrrolidone and N,N-dimethylformamide; the reaction is conducted at a temperature of 80-140° C.; and the mole ratio of 3-fluoro-N'-hydroxy-4-hydroxymethyl benzamidine as shown in formula 1-3 to 4-isobutyl benzoicacid as shown in formula 1-4 is 1:1-2.0.

Preferably, in step (1), the reaction solvent is N,N-dimethylformamide;
preferably, the reaction temperature is 130-140° C.; and
preferably, the mole ratio of 3-fluoro-N'-hydroxy-4-hydroxymethyl benzamidine as shown in formula 1-3 to 4-isobutyl benzoicacid as shown in formula 1-4 is 1:1-1.5, more preferably 1:1-1.2.

According to preferred embodiments of the present invention, the reaction of step (2) is carried out in a reaction solvent which is one or more selected from toluene, tetrahydrofuran and ethyl acetate; the ratio of 2-fluoro-4-[5-(4-isobutylphenyl)-1,2,4-oxadiazol-3-yl]-benzyl alcohol as shown in formula 1-5 (in g, by weight) to the reaction solvent (in ml, by volume) is 1:10-30; the reaction is conducted at a temperature of 40-70° C.; and the mole ratio of 2-fluoro-4-[5-(4-isobutylphenyl)-1,2,4-oxadiazol-3-yl]-benzyl alcohol as shown in formula 1-5 to manganese dioxide is 1:4-10.

Preferably, in step (2), the reaction solvent is ethyl acetate; preferably, the ratio of 2-fluoro-4-[5-(4-isobutylphenyl)-1,2,4-oxadiazol-3-yl]-benzyl alcohol as shown in formula 1-5 (in g, by weight) to the reaction solvent (in ml, by volume) is 1:10;
preferably, the reaction temperature is 60-70° C.; and
preferably, the mole ratio of 2-fluoro-4-[5-(4-isobutylphenyl)-1,2,4-oxadiazol-3-yl]-benzyl alcohol as shown in formula 1-5 to manganese dioxide is 1:5-6, more preferably 1:6.

According to preferred embodiments of the present invention, the reaction of step (3) is carried out in a reaction solvent which is selected from tetrahydrofuran and/or methanol; the mole ratio of 2-fluoro-4-[5-(4-isobutylphenyl)-1,2,4-oxadiazol-3-yl]-benzaldehyde as shown in formula 1-6 to azetidine-3-carboxylic acid as shown in formula 1-7 is 1:1-1.2; the mole ratio of 2-fluoro-4-[5-(4-isobutylphenyl)-1,2,4-oxadiazol-3-yl]-benzaldehyde as shown in formula 1-6 to sodium cyanoborohydride is 1:0.5-6; the reaction is conducted at a temperature of 0-30° C. for a reaction period of 1-16 hours.

Preferably, in step (3), the reaction solvent is methanol;
preferably, the mole ratio of 2-fluoro-4-[5-(4-isobutylphenyl)-1,2,4-oxadiazol-3-yl]-benzaldehyde as shown in formula 1-6 to azetidine-3-carboxylic acid as shown in formula 1-7 is 1:1-1.1, more preferably 1:1;

preferably, the sodium cyanoborohydride is dissolved in methanol and dropped into the reaction system at a temperature of 0-20° C., more preferably 15-20° C.;

preferably, the mole ratio of 2-fluoro-4-[5-(4-isobutylphenyl)-1,2,4-oxadiazol-3-yl]-benzaldehyde as shown in formula 1-6 to sodium cyanoborohydride is 1:1;

preferably, the reaction temperature is 10-20° C., more preferably 15-20° C.; and preferably, the reaction period is 4-16 hours.

In step (1) of synthesis method of the compound represented by formula IB (compound 2) provided by the present invention, the purification of the intermediate crude product is preferably conducted with crystallization, rather than column chromatography. The purification operation will be simplified and the use of large amounts of solvents will be avoided by abandoning column chromatography which needs large amounts of solvents, is less friendly to the environment and has a higher cost. Meanwhile, the reactants, solvents and the amounts thereof used in each step of the method provided by present invention are also adjusted. For example, in step (2), a reduced amount of manganese dioxide can be used for decreasing the cost; and it is ethyl acetate, rather than tetrahydrofuran, used as the reaction solvent for avoiding safety risk that may arise. In step (3), methanol is used as the reaction solvent, which can reduce by-product generation during the reaction, increase the yield of the reaction and reduce the amount of the solvent used in the reaction. Generally speaking, cost is decreased and manufacture on a large scale with a low cost, and high efficiency and safety level is realized through those improvements.

All publications, including but not limited to patents and patent applications cited in this specification are herein incorporated by reference as if each individual publication were specifically and individually indicated to be incorporated by reference herein as though fully set forth.

BRIEF DESCRIPTION OF THE DRAWINGS

Hereinafter, embodiments of the present invention will be described with reference to the accompanying drawings in detail, wherein.

DETAILED DESCRIPTION OF PREFERRED EMBODIMENTS

Figure 1A:
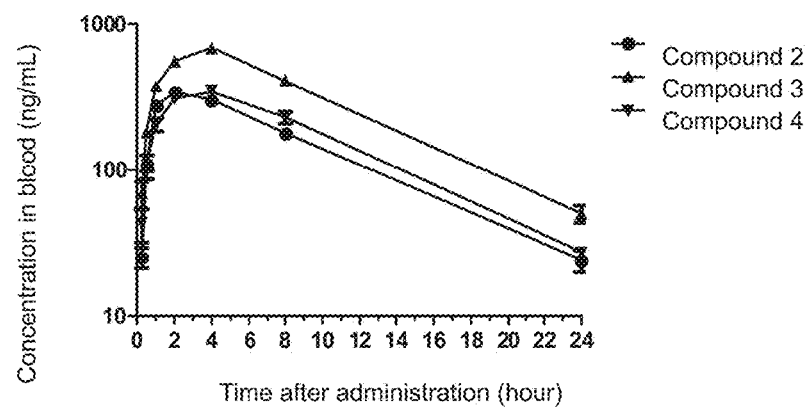
FIGS. 1A and 1B show results from pharmacokinetic experiments of the compounds provided by present invention in Example 6, with FIG. 1A showing data on drug concentration in vivo varied over time in rats after compound 2, 3 and 4 were administered orally, and FIG. 1B showing data on drug concentration in vivo varied over time in rats after compound 1 and 5 were administered orally.

The present invention will be further described in detail in combination with the embodiments hereinafter. It will be appreciated by those skilled in the art that the embodiments provided are only used to illustrate the present invention, rather than limiting the scope of the present invention in any way.

Experimental methods in the following embodiments, if no any other special instruction is provided, are all conventional methods. Raw materials, reagents and other materials used in the following examples, if no any other special instruction is provided, can be commercially available.

Example 1

Synthesis of 1-{4-[5-(4-isobutylphenyl)-1,2,4-oxadiazol-3-yl]-benzyl}-3-azetidine carboxylic acid (Compound 1)

1.1 (Z)—N'-hydroxy-4-hydroxymethyl benzamidine (1-3)

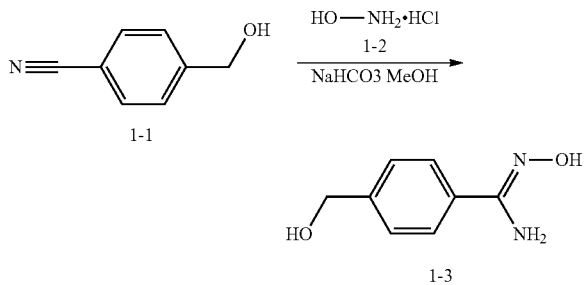

Hydroxylamine hydrochloride (1-2, 20.903 g, 300.76 mmol) and sodium bicarbonate (50.5 g, 601.5 mmol) were added successively to a solution of 4-hydroxymethyl benzonitrile (1-1, 20 g, 150.38 mmol) in methanol (250 mL) to obtain a suspension which was then heated to reflux for 5 hours. It was then cooled down to room temperature and filtered. The filter cake was washed with methanol (100 mL), and the obtained filtrate was concentrated to obtain (Z)—N'-hydroxy-4-hydroxymethyl benzamidine which was a white crude product (1-3, 24.8 g of the crude product, 99.3% yield), which was directly used in the next step. The molecular ion peak shown by liquid chromatography-mass spectrometry was: MS (ESI): m/z 167.3 [M+H]$^+$. NMR: $^1$HNMR (400 MHz, CD3OD) δ: 7.64 (d, J=8.0 Hz, 2H), 7.40 (d, J=8.0 Hz, 2H), 4.65 (s, 2H).

1.2 4-[5-(4-isobutylphenyl)-1,2,4-oxadiazol-3-yl]-benzyl alcohol (1-5)

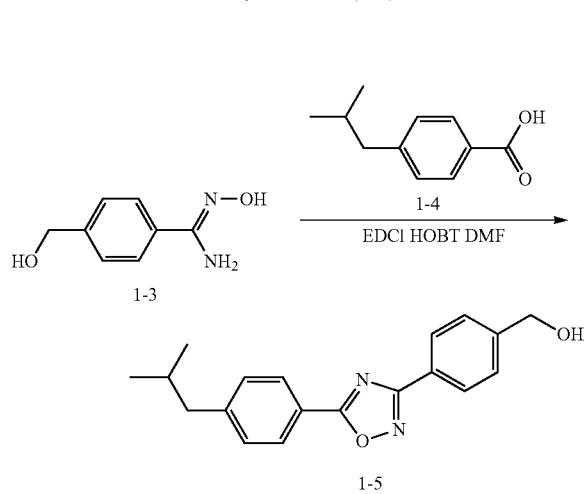

At room temperature, a solution of 4-isobutyl benzoic acid (1-4, 26.6 g, 149.4 mmol), 1-(3-dimethylaminopropyl)-3-ethylcarbodiimide hydrochloride (EDCI, 28.685 g, 149.4 mmol) and 1-hydroxybenzotrizole (20.169 g, 149.4 mmol) in N,N-dimethylformamide (200 mL) was stirred for 30 min before the addition of (Z)—N'-hydroxy-4-hydroxymethyl benzamidine (1-3, 24.8 g, 149.4 mmol). The obtained mixed system was heated in 140° C. oil bath for 2 hours. LC-MS indicated that the reaction was complete. It was then cooled down to room temperature and most of N,N-dimethylformamide was removed by distillation under reduced pressure. The reaction system was extracted with water and ethyl acetate, and the obtained organic phase was washed successively with 0.5N HCl solution, saturated $NaHCO_3$ solution and water, dried with anhydrous sodium sulfate and filtered, then the filtrate was concentrated to dryness. The residue was then purified by column chromatography (elution system:petroleum ether:ethyl acetate=10/1–4/1) to obtain 4-[5-(4-isobutylphenyl)-1,2,4-oxadiazol-3-yl]-benzyl alcohol which was a white solid product (1-5, 34.5 g, 75% yield). The molecular ion peak shown by liquid chromatography-mass spectrometry was: MS (ESI): m/z 309.0 $[M+H]^+$. NMR: $^1$HNMR (400 MHz, CDCl3) δ: 8.16 (d, J=8.4 Hz, 2H), 8.12 (d, J=8.4 Hz, 2H), 7.51 (d, J=8.4 Hz, 2H), 7.33 (d, J=8.4 Hz, 2H), 4.79 (d, J=5.2 Hz, 2H), 2.57 (d, J=7.2 Hz, 2H), 1.95 (m, 1H), 1.85 (t, 1H), 0.97 (d, J=7.2 Hz, 6H).

1.3 4-[5-(4-isobutylphenyl)-1,2,4-oxadiazol-3-yl]-benzaldehyde (1-6)

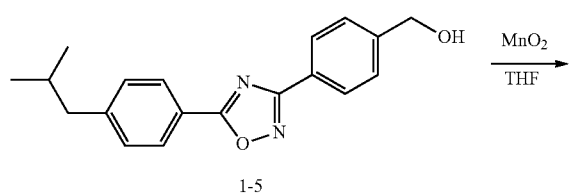

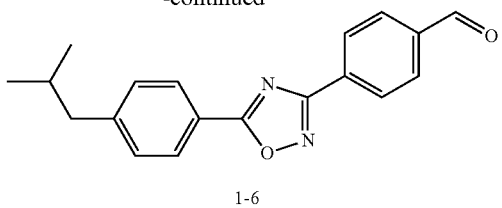

At 60° C., a suspension system of 4-[5-(4-isobutylphenyl)-1,2,4-oxadiazol-3-yl]-benzyl alcohol (1-5, 17.7 g, 57.5 mmol) and manganese dioxide (50 g, 575 mmol) in tetrahydrofuran (330 mL) was stirred for 2 hours. Then the suspension system was cooled to room temperature, filtered and concentrated to dryness. The residue was then purified by column chromatography (elution system:petroleum ether:ethyl acetate=20/1) to obtain 4-[5-(4-isobutylphenyl)-1,2,4-oxadiazol-3-yl]-benzaldehyde which was a white solid product (1-6, 16.44 g, 93.5% yield). The molecular ion peak shown by liquid chromatography-mass spectrometry was: MS (ESI): m/z 307.2 $[M+H]^+$.

2. 1-{4-[5-(4-isobutylphenyl)-1,2,4-oxadiazol-3-yl]-benzyl}-3-azetidine carboxylic acid

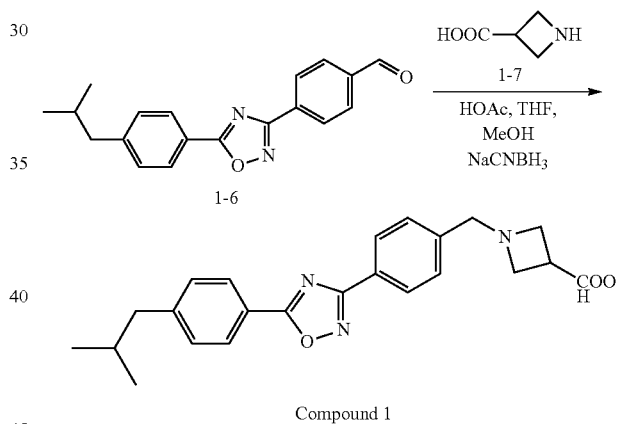

Compound 1

At room temperature, a solution of 4-[5-(4-isobutylphenyl)-1,2,4-oxadiazol-3-yl]-benzaldehyde (1-6, 10 g, 32.7 mmol), azetidine-3-carboxylic acid (1-7, 3.63 g, 36 mmol) and acetic acid (15 mL) in methanol-tetrahydrofuran (200 mL/200 mL) was stirred for 2 hours. Then a solution of sodium cyanoborohydride (1.03 g, 16.35 mmol) in methanol (60 mL) was added to the reaction mixture and the resulting mixture was stirred at room temperature for additional 16 hours and filtered. The filter cake was washed with methanol (90 mL) and then dried to obtain 1-{4-[5-(4-isobutylphenyl)-1,2,4-oxadiazol-3-yl]-benzyl}-3-azetidine carboxylic acid which was a white solid product (5.5 g; reduction product 1-5 from compound 1-6 was collected, and then oxidized and reductive aminated to obtain 5 g final product; 82% yield). The molecular ion peak shown by liquid chromatography-mass spectrometry was: MS (ESI): m/z 392.2 $[M+H]^+$. NMR: $^1$HNMR (400 MHz, CD3OD) δ: 8.23 (d, J=8.4 Hz, 2H), 8.15 (d, J=8.0 Hz, 2H), 7.64 (d, J=8.4 Hz, 2H), 7.44 (d, J=8.0 Hz, 2H), 4.34 (s, 2H), 4.12 (m, 4H), 3.42 (m, 1H), 2.63 (d, J=7.2 Hz, 2H), 1.97 (m, 1H) 0.97 (d, J=7.2 Hz, 6H).

Example 2

Synthesis of 1-{2-fluoro-4-[5-(4-isobutylphenyl)-1,2,4-oxadiazol-3-yl]-benzyl}-3-azetidine carboxylic acid (Compound 2)

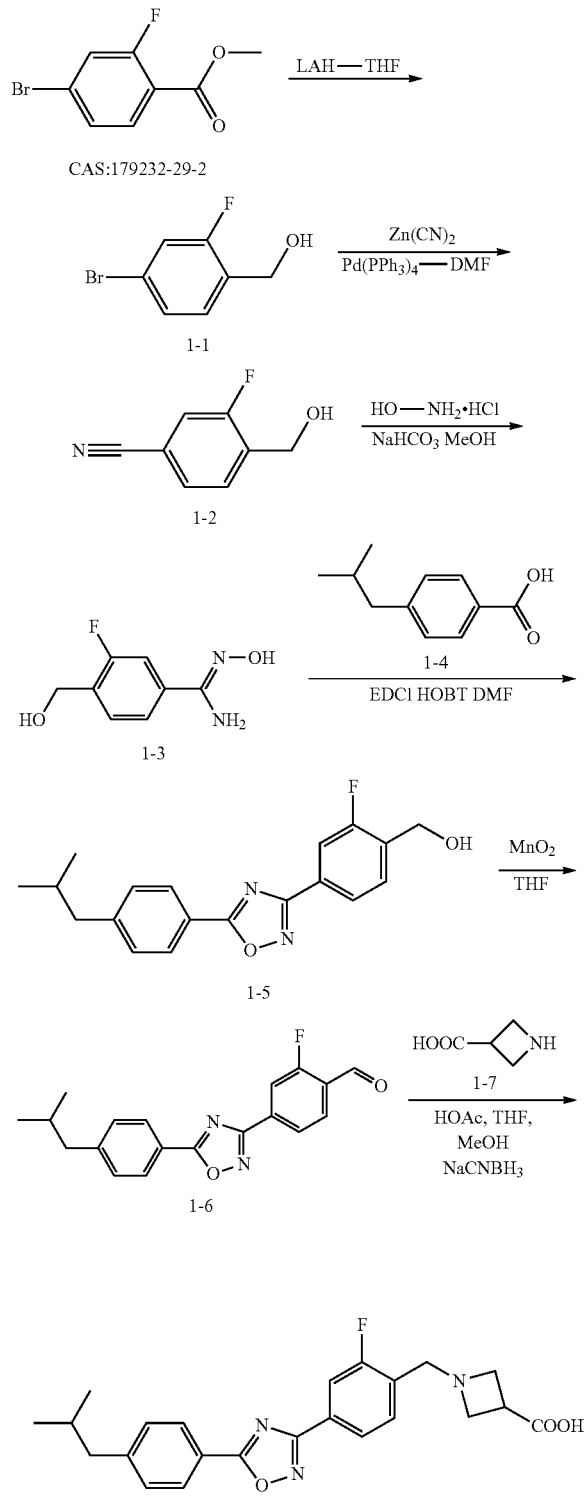

1.1 4-bromo-2-fluorobenzyl alcohol (1-1)

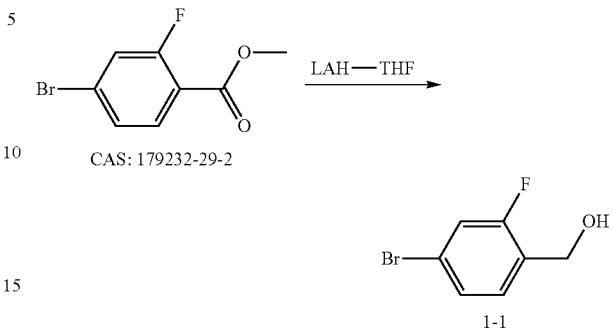

At 0° C., lithium aluminum hydride (1.14 g, 30 mmol) was dropped into a solution of Methyl 4-Bromo-2-fluorobenzoate (4.66 g, 20 mmol) in tetrahydrofuran (100 mL) slowly. The ice-salt bath used was removed after that dropping. The reaction was complete (detected by LCMS and TLC) after stirred for 1 hour at room temperature. The mixture was cooled to 0° C. again and the reaction was quenched with water (1.14 mL) and 10% NaOH solution (11.4 mL) respectively. After stirred for 15 min at room temperature, the mixture was filtered and then the filter cake was washed with tetrahydrofuran (50 mL×2) and ethyl acetate EA (50 mL×2). The filtrate was dried with anhydrous sodium sulfate, filtered, and then concentrated to obtain a colorless oil product (3.4 g, 83% yield).

1.2 3-fluoro-4-hydroxymethyl benzonitrile (1-2)

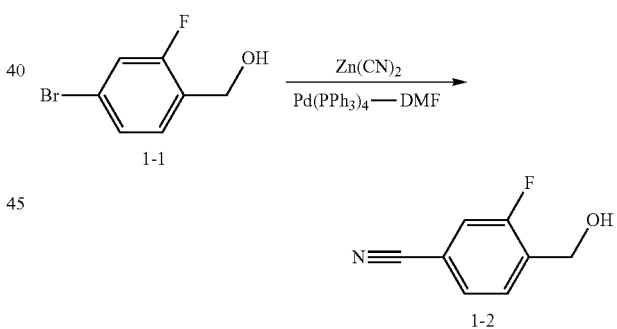

Zinc cyanide (1.85 g, 15.85 mmol) and tetrakis(triphenylphosphine) palladium (Pd(PPh$_3$)$_4$, 0.916 g, 0.79 mmol) were added into a solution of 4-bromo-2-fluorobenzyl alcohol (1-1, 3.25 g, 15.85 mmol) in DMF (35 mL). After deoxygenated via argon bubbling, the reaction mixture was heated at 100° C. and reacted for 16 hours, cooled down to room temperature, diluted with ethyl acetate (100 mL), washed successively with water (100 mL×3) and saturated brine (100 mL×3), dried with anhydrous sodium sulfate and filtered. The filtrate was concentrated to obtain a crude product. The crude product was then purified by column chromatography (elution system:petroleum ether:ethyl acetate=15/1–4/1) to obtain a white solid product (0.72 g, 30% yield). The molecular ion peak shown by liquid chromatography-mass spectrometry was: MS (ESI): m/z 152.1 [M+H]$^+$. NMR: $^1$HNMR (400 MHz, CDCl3) δ: 7.63 (t, J=7.6 Hz, 8.0 Hz, 1H), 7.48 (dd, J=1.2 Hz, 8.0 Hz, 1H), 7.48 (dd, J=1.2 Hz, 9.2 Hz, 1H), 4.83 (d, J=10 Hz, 2H), 2.00 (t, J=10 Hz, 1H).

1.3 (Z)-3-fluoro-N'-hydroxy-4-hydroxymethyl benzamidine (1-3)

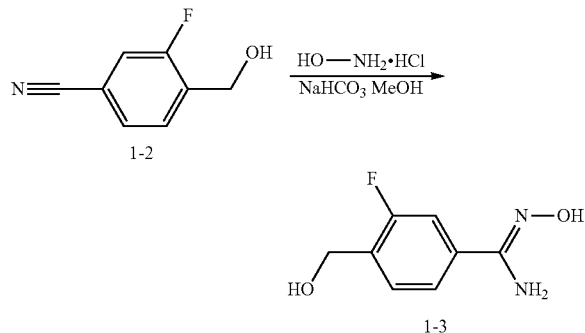

Hydroxylamine hydrochloride (0.645 g, 9.28 mmol) and sodium bicarbonate (1.56 g, 18.56 mmol) were added successively to a solution of 3-fluoro-4-hydroxymethyl benzonitrile (1-2, 0.70 g, 4.64 mmol) in methanol (150 mL) to obtain a suspension which was then heated to reflux for 5 hours. It was then cooled down to room temperature and filtered. The filter cake was washed with methanol (10 mL), and the obtained filtrate was concentrated to obtain 3-fluoro-N'-hydroxy-4-hydroxymethyl benzamidine which was a white crude product (1-3, 0.846 g, 99% yield), which was directly used in the next step. The molecular ion peak shown by liquid chromatography-mass spectrometry was: MS (ESI): m/z 185.0 [M+H]$^+$. NMR: $^1$HNMR (400 MHz, CD3OD) δ: 7.51~7.45 (m, 2H), 7.37~7.34 (m, 1H), 4.67 (s, 2H).

1.4 2-fluoro-4-[5-(4-isobutylphenyl)-1,2,4-oxadiazol-3-yl]-benzyl alcohol (1-5)

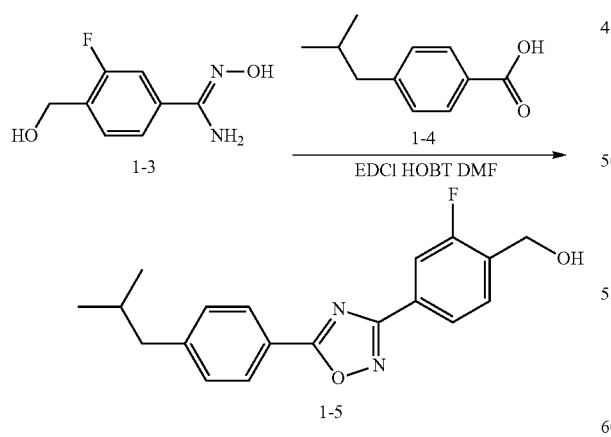

At room temperature, a solution of 4-isobutyl benzoicacid (1-4, 0.819 g, 4.60 mmol), 1-(3-dimethylaminopropyl)-3-ethylcarbodiimide hydrochloride (EDCI, 0.882 g, 4.60 mmol) and 1-hydroxybenzotrizole (0.621 g, 4.60 mmol) in N,N-dimethylformamide (10 mL) was stirred for 30 min before the addition of (Z)-3-fluoro-N'-hydroxy-4-hydroxymethyl benzamidine (1-3, 0.846 g, 4.60 mmol). The mixed system was heated in 140° C. oil bath for 2 hours. LCMS indicated that starting materials reacted completely. It was then cooled down to room temperature and most of N,N-dimethylformamide was removed by distillation under reduced pressure. The mixture was extracted with water and ethyl acetate, and the obtained organic phase was washed successively with 0.5N HCl solution, saturated NaHCO$_3$ solution and water, dried with anhydrous sodium sulfate and filtered, then the filtrate was concentrated to dryness. The residue was then purified by column chromatography (elution system:petroleum ether:ethyl acetate=10/1–4/1) to obtain 2-fluoro-4-[5-(4-isobutylphenyl)-1,2,4-oxadiazol-3-yl]-benzyl alcohol which was a white solid product (1-5, 0.92 g, 61% yield). The molecular ion peak shown by liquid chromatography-mass spectrometry was: MS (ESI): m/z 327.0 [M+H]$^+$. NMR: $^1$HNMR (400 MHz, CDCl3) δ: 8.11 (d, J=8.0 Hz, 2H), 7.98 (m, 1H), 7.86 (m, 1H), 7.59 (t, J=8.0 Hz, 7.6 Hz, 1H), 7.33 (d, J=8.0 Hz, 2H), 4.85 (s, 2H), 2.57 (d, J=6.8 Hz, 2H), 1.93 (m, 1H), 0.93 (d, J=6.8 Hz, 6H),

1.5 2-fluoro-4-[5-(4-isobutylphenyl)-1,2,4-oxadiazol-3-yl]-benzaldehyde (1-6)

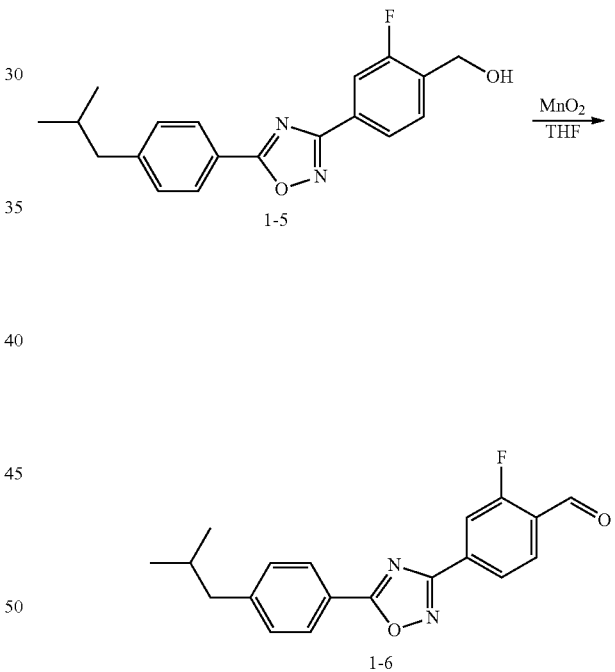

At 60° C., a suspension system of 2-fluoro-4-[5-(4-isobutylphenyl)-1,2,4-oxadiazol-3-yl]-benzyl alcohol (1-5, 0.91 g, 2.79 mmol) and manganese dioxide (2.43 g, 27.9 mmol) in tetrahydrofuran (30 mL) was stirred for 2 hours. Then the suspension system was cooled down to room temperature, filtered and concentrated to obtain 2-fluoro-4-[5-(4-isobutylphenyl)-1,2,4-oxadiazol-3-yl]-benzaldehyde which was a white solid product (1-6, 0.90 g, 99.6% yield). The molecular ion peak shown by liquid chromatography-mass spectrometry was: MS (ESI): m/z 325.0 [M+H]$^+$. NMR: $^1$HNMR (400 MHz, CDCl3) δ: 10.42 (s, 1H), 8.12~7.99 (m, 5H), 7.34 (d, J=7.2 Hz, 2H), 2.58 (d, J=6.4 Hz, 2H), 1.93 (m, 1H), 0.93 (d, J=6.4 Hz, 6H).

1.6 1-{2-fluoro-4-[5-(4-isobutylphenyl)-1,2,4-oxadiazol-3-yl]-benzyl}-3-azetidine carboxylic acid (Compound 2)

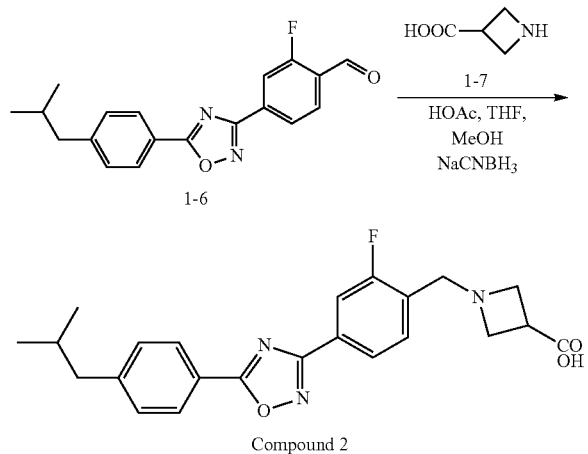

Compound 2

At room temperature, a solution of 2-fluoro-4-[5-(4-isobutylphenyl)-1,2,4-oxadiazol-3-yl]-benzaldehyde (1-6, 0.90 g, 2.78 mmol), azetidine-3-carboxylic acid (1-7, 0.28 g, 2.78 mmol) and acetic acid (1 mL) in methanol-tetrahydrofuran (20 mL/20 mL) was stirred for 2 hours. Then a solution of sodium cyanoborohydride (1.03 g, 16.35 mmol) in methanol (60 mL) was added to the reaction mixture and the resulting mixture was stirred at room temperature for additional 16 hours and filtered. The filter cake was washed with methanol (10 mL) and then dried to obtain 1-{2-fluoro-4-[5-(4-isobutylphenyl)-1,2,4-oxadiazol-3-yl]-benzyl}-3-azetidine carboxylic acid (Compound 2) which was a white solid product (0.20 g, 18% yield). The molecular ion peak shown by liquid chromatography-mass spectrometry was: MS (ESI): m/z 410.0 [M+H]$^+$. NMR: $^1$HNMR (400 MHz, CD3OD) δ: 8.13 (d, J=8.4 Hz, 2H), 8.05 (m, 1H), 7.97 (m, 1H), 7.68 (t, J=8.0 Hz, 7.6 Hz, 1H), 7.42 (d, J=8.4 Hz, 2H), 4.40 (s, 2H), 4.15 (m, 4H), 3.41 (m, 1H), 2.61 (d, J=7.2 Hz, 2H), 1.95 (m, 1H), 0.94 (d, J=7.2 Hz, 6H).

Example 3

Synthesis of 1-{2-chloro-4-[5-(4-isobutylphenyl)-1,2,4-oxadiazol-3-yl]-benzyl}-3-azetidine carboxylic acid (Compound 3)

1.1 Methyl 4-bromo-2-chlorobenzoate (185312-82-7)

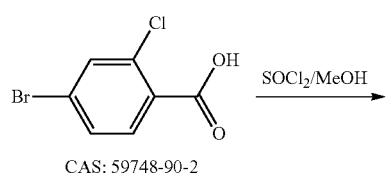

CAS: 59748-90-2

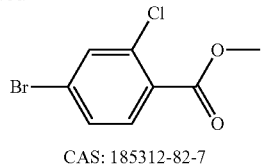

CAS: 185312-82-7

At 0° C., thionyl chloride (3.57 g, 30 mmol) was added dropwise into a solution of 4-bromo-2-chlorobenzoic acid (4.71 g, 20 mmol) in methanol (100 mL) slowly. The ice-salt bath used was removed after that dropping and then the reaction mixture was heated to reflux for 3 hours. TLC and LCMS indicated that starting materials reacted completely. The solvent and excess thionyl chloride were removed by rotary evaporation to give a crude product. Then the crude product was dissolved in dichloromethane (100 mL), washed successively with saturated sodium bicarbonate solution (100 mL×2) and saturated brine (100 mL), dried with anhydrous sodium sulfate and filtered. A yellow solid product (4.79 g, 96% yield) was obtained by rotary evaporation. The molecular ion peak shown by liquid chromatography-mass spectrometry was: MS (ESI): m/z 248.9.8/250.8/252.8 [M+H]$^+$.

1.2 4-bromo-2-chlorobenzyl alcohol (1-1)

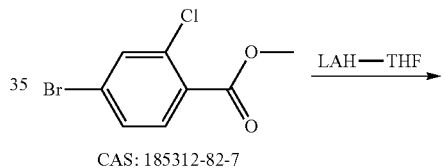

CAS: 185312-82-7

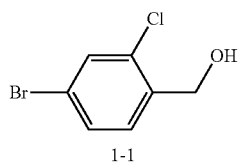

1-1

At 0° C., lithium aluminum hydride (1.09 g, 30 mmol) was dropped into a solution of methyl 4-bromo-2-chlorobenzoate (4.78 g, 19.16 mmol) in tetrahydrofuran (100 mL) slowly. The ice-salt bath used was removed after that dropping. The reaction was complete (detected with LCMS and TLC) after stirred for 1 hour at room temperature. The mixture was cooled to 0° C. again and the reaction was quenched with water (1.09 mL) and 10% NaOH solution (10.9 mL) respectively. After stirred for 15 min at room temperature, the mixture was filtered and then the filter cake was washed with tetrahydrofuran (50 mL×2) and ethyl acetate EA (50 mL×2). The filtrate was dried with anhydrous sodium sulfate, filtered, and then concentrated to obtain a colorless oil product (3.4 g, 80% yield). The molecular ion peak shown by liquid chromatography-mass spectrometry was: MS (ESI): m/z 202.9/204.9 [M–OH]$^+$.

1.3 3-chloro-4-hydroxymethyl benzonitrile (1-2)

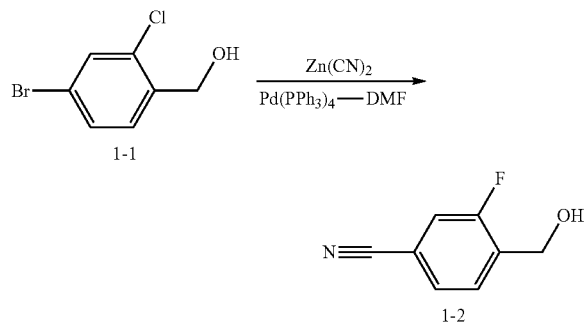

Zinc cyanide (0.67 g, 5.73 mmol) and tetrakis(triphenylphosphine) palladium (Pd(PPh₃)₄, 0.33 g, 0.287 mmol) were added into a solution of 4-bromo-2-chlorobenzyl alcohol (1-1, 1.27 g, 5.73 mmol) in DMF (15 mL). After deoxygenated via argon bubbling, the reaction mixture was heated at 100° C. and reacted for 16 hours, cooled down to room temperature, diluted with ethyl acetate (50 mL), washed successively with water (50 mL×3) and saturated brine (50 mL×3), dried with anhydrous sodium sulfate and filtered. The filtrate was concentrated to obtain a crude product. The crude product was then purified by column chromatography (elution system:petroleum ether:ethyl acetate=15/1–4/1) to obtain a white solid product (0.387 g, 40% yield). The molecular ion peak shown by liquid chromatography-mass spectrometry was: MS (ESI): m/z 168.0/170.1 [M+H]⁺.

1.4 (Z)-3-chloro-N'-hydroxy-4-hydroxymethyl benzamidine (1-3)

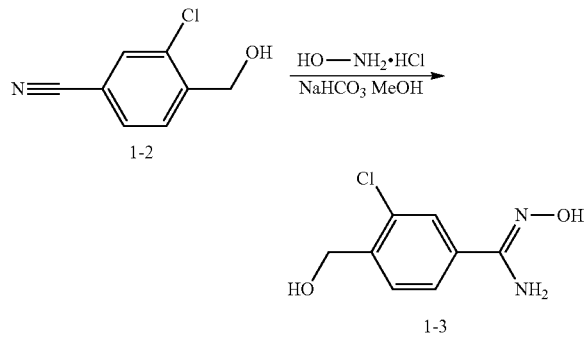

Hydroxylamine hydrochloride (0.321 g, 4.62 mmol) and sodium bicarbonate (0.776 g, 9.24 mmol) were added successively to a solution of 3-chloro-4-hydroxymethyl benzonitrile (1-2, 0.387 g, 2.31 mmol) in methanol (80 mL) to obtain a suspension which was then heated to reflux for 5 hours. It was then cooled down to room temperature and filtered. The filter cake was washed with methanol (10 mL), and the obtained filtrate was concentrated to obtain, as a white crude product, 3-chloro-N'-hydroxy-4-hydroxymethyl benzamidine (1-3, 0.324 g, 70% yield), which was directly used in the next step. The molecular ion peak shown by liquid chromatography-mass spectrometry was: MS (ESI): m/z 201 [M+H]⁺. NMR: ¹HNMR (400 MHz, DMSO-d6) δ: 9.74 (br, 1H), 7.68 (s, 1H), 7.67 (d, J=8.4 Hz, 1H), 7.54 (d, J=8.4 Hz, 1H), 5.88 (br, 2H), 5.49 (br, 1H), 4.27 (s, 2H).

1.5 2-chloro-4-[5-(4-isobutylphenyl)-1,2,4-oxadiazol-3-yl]-benzyl alcohol (1-5)

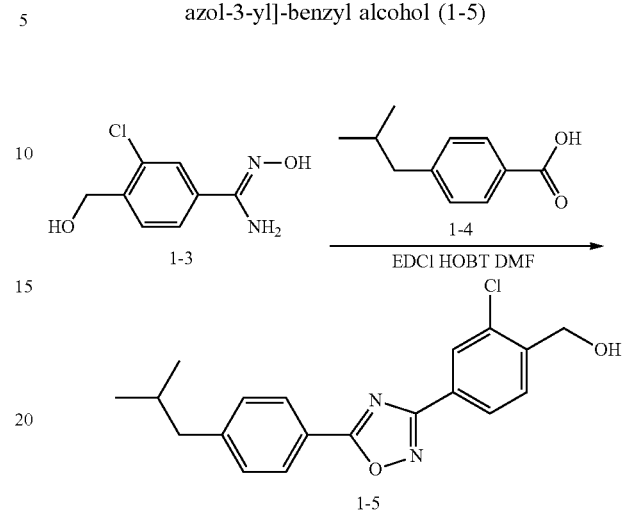

At room temperature, a solution of 4-isobutyl benzoicacid (1-4, 0.288 g, 1.62 mmol), 1-(3-dimethylaminopropyl)-3-ethylcarbodiimide hydrochloride (EDCI, 0.31 g, 1.62 mmol) and 1-hydroxybenzotrizole (0.219 g, 1.62 mmol) in N,N-dimethylformamide (8 mL) was stirred for 30 min before the addition of (Z)-3-chloro-N'-hydroxy-4-hydroxymethyl benzamidine (1-3, 0.324 g, 1.21 mmol). The obtained mixed system was heated in 140° C. oil bath for 2 hours. LCMS indicated that starting materials reacted completely. It was then cooled down to room temperature and most of N,N-dimethylformamide was removed by distillation under reduced pressure. The mixture was extracted with water and ethyl acetate, and the organic phase obtained was washed successively with 0.5N HCl solution, saturated NaHCO₃ solution and water, dried with anhydrous sodium sulfate and filtered, then the filtrate was concentrated to dryness. The residue was then purified by column chromatography (elution system:petroleum ether:ethyl acetate=10/1–4/1) to obtain 2-chloro-4-[5-(4-isobutylphenyl)-1,2,4-oxadiazol-3-yl]-benzyl alcohol which was a white solid product (1-5, 0.36 g, 65% yield). The molecular ion peak shown by liquid chromatography-mass spectrometry was: MS (ESI): m/z 343.0/345.0 [M+H]⁺. NMR: ¹HNMR (400 MHz, CDCl3) δ: 8.16 (d, J=1.2 Hz, 1H), 8.10 (d, J=8.4 Hz, 2H), 8.07 (dd, J=1.2 Hz, 8.0 Hz, 1H), 7.66 (d, J=8.0 Hz, 1H), 7.32 (d, J=8.4 Hz, 2H), 4.85 (s, 2H), 2.57 (d, J=7.2 Hz, 2H), 0.94 (d, J=7.2 Hz, 6H).

1.6 2-chloro-4-[5-(4-isobutylphenyl)-1,2,4-oxadiazol-3-yl]-benzaldehyde (1-6)

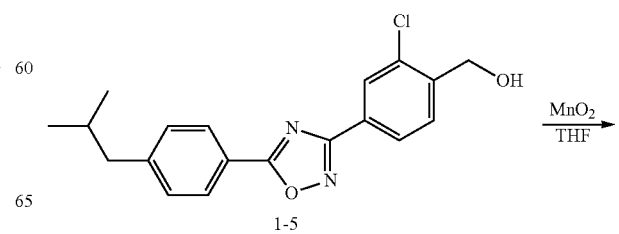

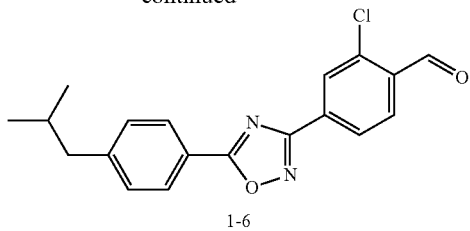

At 40° C., a suspension system of 2-chloro-4-[5-(4-isobutylphenyl)-1,2,4-oxadiazol-3-yl]-benzyl alcohol (1-5, 0.36 g, 1.05 mmol) and manganese dioxide (0.914 g, 10.5 mmol) in tetrahydrofuran (30 mL) was stirred for 2 hours. Then the suspension system was cooled down to room temperature, filtered and concentrated to obtain a crude product. The crude product was purified by column chromatography (elution system:petroleum ether:ethyl acetate=20/1–10/1) to obtain 2-chloro-4-[5-(4-isobutylphenyl)-1,2,4-oxadiazol-3-yl]-benzaldehyde (1-6, 0.34 g, 95% yield). The molecular ion peak shown by liquid chromatography-mass spectrometry was: MS (ESI): m/z 341.1 [M+H]$^+$. NMR: $^1$HNMR (400 MHz, CDCl3) δ: 10.52 (s, 1H), 8.28 (d, J=1.2 Hz, 1H), 8.16 (dd, J=1.2 Hz, 8.4 Hz, 1H), 8.10 (d, J=8.4 Hz, 2H), 8.04 (d, J=8.4 Hz, 1H), 7.33 (d, J=8.4 Hz, 2H), 2.58 (d, J=7.6 Hz, 2H), 0.94 (d, J=7.6 Hz, 6H).

1.7 1-{2-chloro-4-[5-(4-isobutylphenyl)-1,2,4-oxadiazol-3-yl]-benzyl}-3-azetidine carboxylic acid (Compound 3)

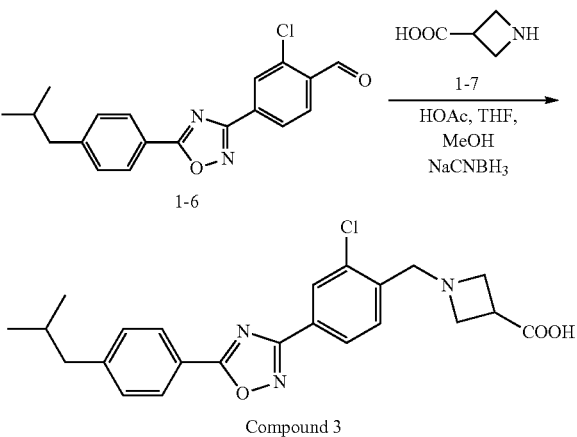

At room temperature, a solution of 2-chloro-4-[5-(4-isobutylphenyl)-1,2,4-oxadiazol-3-yl]-benzaldehyde (1-6, 0.34 g, 1.0 mmol), azetidine-3-carboxylic acid (1-7, 0.101 g, 1.0 mmol) and acetic acid (0.35 mL) in methanol-tetrahydrofuran (10 mL/10 mL) was stirred for 2 hours. Then a solution of sodium cyanoborohydride (0.378 g, 6.0 mmol) in methanol (20 mL) was added to the reaction mixture and the resulting mixture was stirred at room temperature for additional 16 hours and filtered. The filter cake was washed with methanol (10 mL) and then dried to obtain 1-{2-chloro-4-[5-(4-isobutylphenyl)-1,2,4-oxadiazol-3-yl]-benzyl}-3-azetidine carboxylic acid (Compound 3) which was a white solid product (0.109 g, 26% yield). The molecular ion peak shown by liquid chromatography-mass spectrometry was: MS (ESI): m/z 426.1/428.3 [M+H]$^+$. NMR: $^1$HNMR (400 MHz, CD3OD) δ: 8.33 (d, J=1.6 Hz, 1H), 8.22 (dd, J=1.6 Hz, 8.0 Hz, 1H), 8.16 (d, J=8.0 Hz, 2H), 7.76 (d, J=8.0 Hz, 1H), 7.45 (d, J=8.0 Hz, 2H), 4.72 (s, 2H), 4.46 (m, 4H), 3.74 (m, 1H), 2.63 (d, J=7.2 Hz, 2H), 1.97 (m, 1H), 0.96 (d, J=7.2 Hz, 6H).

Example 4

Synthesis of 1-{2-bromo-4-[5-(4-isobutylphenyl)-1,2,4-oxadiazol-3-yl]-benzyl}-3-azetidine carboxylic acid (Compound 4)

1.1 Methyl 2,4-dibromobenzoate (54335-33-0)

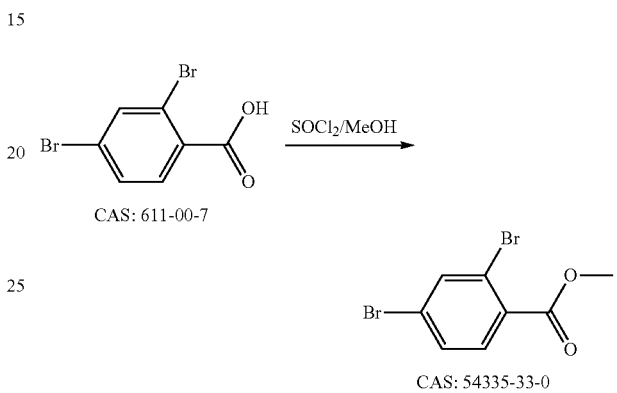

At 0° C., thionyl chloride (3.57 g, 30 mmol) was added dropwise into a solution of 2,4-dibromobenzoicacid (5.60 g, 20 mmol) in methanol (100 mL) slowly. The ice-salt bath used was removed after that dropping and then the reaction mixture was heated to reflux for 3 hours. TLC and LCMS indicated that starting materials reacted completely. The solvent and excess thionyl chloride were removed by rotary evaporation to give a crude product. Then the crude product was dissolved in dichloromethane (100 mL), washed successively with saturated sodium bicarbonate solution (100 mL×2) and saturated brine (100 mL), dried with anhydrous sodium sulfate and filtered. A yellow solid product (5.92 g, 100% yield) was obtained by rotary evaporation. The molecular ion peak shown by liquid chromatography-mass spectrometry was: MS (ESI): m/z 292.8/294.7/269.9 [M+H]$^+$.

1.2 2,4-dibromobenzyl alcohol (1-1)

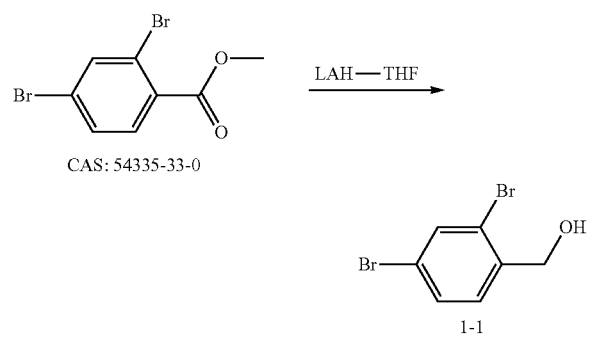

At 0° C., lithium aluminum hydride (1.14 g, 30 mmol) was dropped into a solution of methyl 2,4-dibromobenzoate (5.90 g, 20 mmol) in tetrahydrofuran (120 mL) slowly. The ice-salt bath used was removed after that dropping. The reaction was complete (detected with LCMS and TLC) after stirred for 1 hour at room temperature. The mixture was cooled to 0° C. again and the reaction was quenched with water (1.14 mL) and 10% NaOH solution (11.4 mL) respectively. After stirred for 15 min at room temperature, the mixture was filtered and then the filter cake was washed with tetrahydrofuran (60 mL×2) and ethyl acetate EA (60 mL×2). The filtrate was dried with anhydrous sodium sulfate, filtered, concentrated, and then purified by column chromatography (elution system:petroleum ether:ethyl acetate=10/1–4/1) to obtain a colorless oil product (2.3 g, 43% yield). The molecular ion peak shown by liquid chromatography-mass spectrometry was: MS (ESI): m/z 246.9/248.9/250.9 [M–OH]$^+$.

1.3 3-bromo-4-hydroxymethyl benzonitrile (1-2)

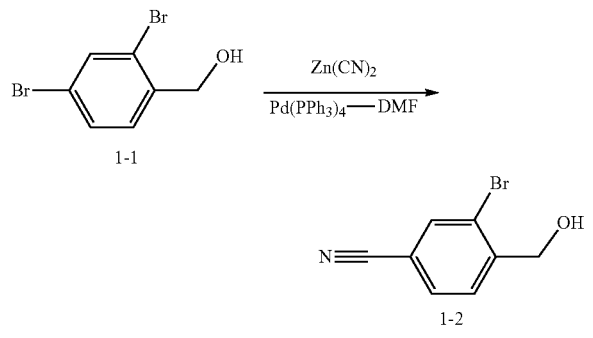

Zinc cyanide (1.01 g, 8.65 mmol) and tetrakis(triphenylphosphine) palladium (Pd(PPh$_3$)$_4$, 0.50 g, 0.43 mmol) were added into a solution of 2,4-dibromobenzyl alcohol (1-1, 2.3 g, 8.65 mmol) in DMF (20 mL). After deoxygenated via argon bubbling, the reaction mixture was heated at 80° C. and reacted for 5 hours, cooled down to room temperature, diluted with ethyl acetate (80 mL), washed successively with water (80 mL×3) and saturated brine (80 mL×3), dried with anhydrous sodium sulfate and filtered. The filtrate was concentrated to obtain a crude product. The crude product was then purified by column chromatography (elution system:petroleum ether:ethyl acetate=15/1–4/1) to obtain a white solid product (0.81 g, 44% yield). The molecular ion peak shown by liquid chromatography-mass spectrometry was: MS (ESI): m/z 211.9/213.9 [M+H]$^+$. NMR: $^1$HNMR (400 MHz, CDCl3) δ: 7.82 (s, 1H), 7.69 (d, J=8.0 Hz, 1H), 7.65 (d, J=8.0 Hz, 1H), 4.80 (s, 2H).

1.4 (Z)-3-bromo-N'-hydroxy-4-hydroxymethyl benzamidine (1-3)

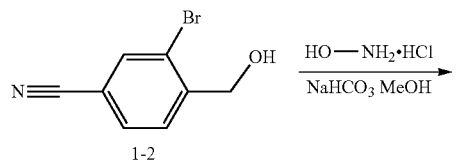

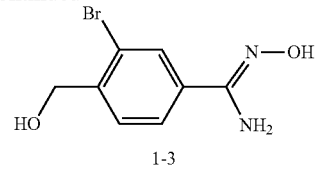

Hydroxylamine hydrochloride (0.524 g, 7.54 mmol) and sodium bicarbonate (1.27 g, 15.08 mmol) were added successively to a solution of 3-bromo-4-hydroxymethyl benzonitrile (1-2, 0.80 g, 3.77 mmol) in methanol (120 mL) to obtain a suspension which was then heated to reflux for 5 hours. It was then cooled down to room temperature and filtered. The filter cake was washed with methanol (10 mL), and the filtrate was concentrated to obtain 3-bromo-N'-hydroxy-4-hydroxymethyl benzamidine which was a white crude product (1-3, 0.90 g, 97% yield), which was directly used in the next step. The molecular ion peak shown by liquid chromatography-mass spectrometry was: MS (ESI): m/z 245/247 [M+H]$^+$.

1.5 2-bromo-4-[5-(4-isobutylphenyl)-1,2,4-oxadiazol-3-yl]-benzyl alcohol (1-5)

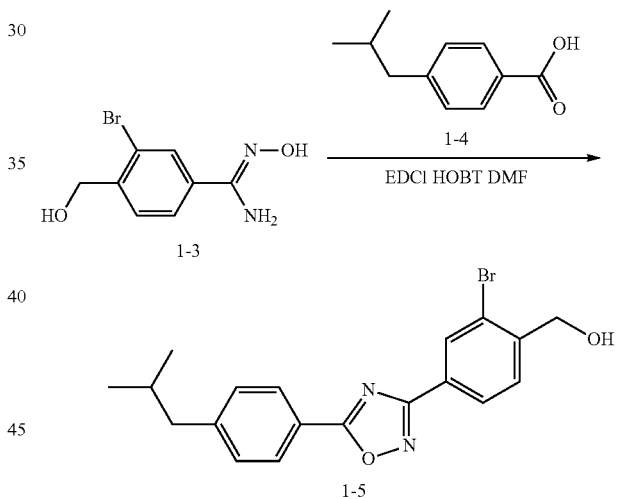

At room temperature, a solution of 4-isobutyl benzoicacid (1-4, 0.653 g, 3.67 mmol), 1-(3-dimethylaminopropyl)-3-ethylcarbodiimide hydrochloride (EDCI, 0.704 g, 3.67 mmol) and 1-hydroxybenzotrizole (0.495 g, 3.77 mmol) in N,N-dimethylformamide (10 mL) was stirred for 30 min before the addition of (Z)-3-bromo-N-hydroxy-4-hydroxymethyl benzamidine (1-3, 0.90 g, 3.67 mmol). The mixed system was heated in 140° C. oil bath for 2 hours. LCMS indicated that starting materials reacted completely. It was then cooled down to room temperature and most of N,N-dimethylformamide was removed by distillation under reduced pressure. The mixture was extracted with water and ethyl acetate, and the obtained organic phase was washed successively with 0.5N HCl solution, saturated NaHCO$_3$ solution and water, dried with anhydrous sodium sulfate and filtered, then the filtrate was concentrated to dryness. The residue was then purified by column chromatography (elution system:petroleum ether:ethyl acetate=10/1–4/1) to obtain 2-bromo-4-[5-(4-isobutylphenyl)-1,2,4-oxadiazol-3-yl]-benzyl alcohol which was a white solid product (1-5, 0.36 g, 36% yield). The molecular ion peak shown by liquid chromatography-mass spectrometry was: MS (ESI): m/z 387.1/389.1 [M+H]$^+$.

1.6 2-bromo-4-[5-(4-isobutylphenyl)-1,2,4-oxadiazol-3-yl]-benzaldehyde (1-6)

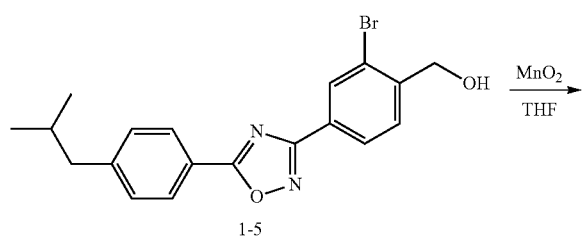

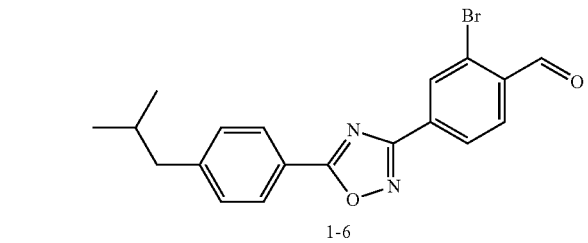

At 50° C., a suspension system of 2-bromo-4-[5-(4-isobutylphenyl)-1,2,4-oxadiazol-3-yl]-benzyl alcohol (1-5, 0.51 g, 1.32 mmol) and manganese dioxide (1.15 g, 13.2 mmol) in tetrahydrofuran (30 mL) was stirred for 2 hours. Then the suspension system was cooled to room temperature, filtered and concentrated to obtain a crude product. The crude product was purified by column chromatography (elution system:petroleum ether:ethyl acetate=20/1~10/1) to obtain 2-bromo-4-[5-(4-isobutylphenyl)-1,2,4-oxadiazol-3-yl]-benzaldehyde (1-6, 0.34 g, 67% yield). The molecular ion peak shown by liquid chromatography-mass spectrometry was: MS (ESI): m/z 385.0/387.0 [M+H]$^+$.

1.7 1-{2-bromo-4-[5-(4-isobutylphenyl)-1,2,4-oxadiazol-3-yl]-benzyl}-3-azetidine carboxylic acid (Compound 4)

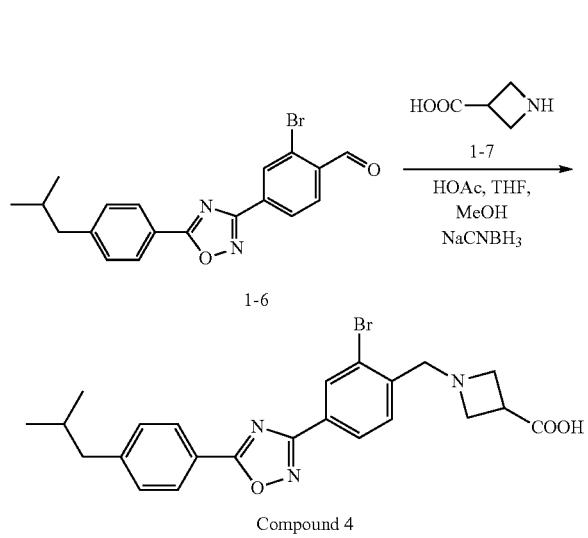

At room temperature, a solution of 2-bromo-4-[5-(4-isobutylphenyl)-1,2,4-oxadiazol-3-yl]-benzaldehyde (1-6, 0.34 g, 0.88 mmol), azetidine-3-carboxylic acid (1-7, 0.089 g, 0.88 mmol) and acetic acid (0.3 mL) in methanol-tetrahydrofuran (10 mL/10 mL) was stirred for 2 hours. Then a solution of sodium cyanoborohydride (0.333 g, 5.28 mmol) in methanol (20 mL) was added to the reaction mixture and the resulting mixture was stirred at room temperature for additional 16 hours and filtered. The filter cake was washed with methanol (10 mL) and then dried to obtain 1-{2-bromo-4-[5-(4-isobutylphenyl)-1,2,4-oxadiazol-3-yl]-benzyl}-3-azetidine carboxylic acid (Compound 4) which was a white solid product (0.1112 g, 27% yield). The molecular ion peak shown by liquid chromatography-mass spectrometry was: MS (ESI): m/z 469.9/471.8 [M+H]$^+$. NMR: $^1$HNMR (400 MHz, CDCl3) δ: 8.39 (d, J=1.2 Hz, 1H), 8.12 (dd, J=1.2 Hz, 8.4 Hz, 1H), 8.08 (d, J=8.4 Hz, 2H), 7.70 (d, J=8.4 Hz, 1H), 7.31 (d, J=8.4 Hz, 2H), 4.23 (s, 2H), 4.08 (m, 2H), 3.99 (m, 2H), 3.44 (m, 1H), 2.56 (d, J=6.8 Hz, 2H), 1.91 (m, 1H), 0.93 (d, J=6.8 Hz, 6H).

Example 5

Synthesis of 1-{2-methyl-4-[5-(4-isobutylphenyl)-1,2,4-oxadiazol-3-yl]-benzyl}-3-azetidine carboxylic acid (Compound 5)

1.1 4-bromo-2-methylbenzyl alcohol (1-1)

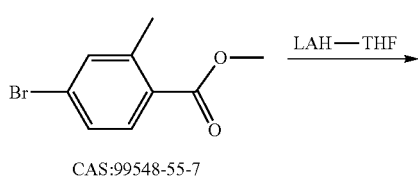

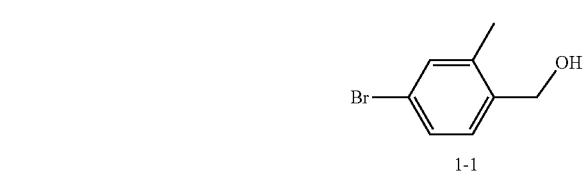

At 0° C., lithium aluminum hydride (1.425 g, 37.5 mmol) was dropped into a solution of methyl 4-bromo-2-methylbenzoate (5.725 g, 25 mmol) in tetrahydrofuran (120 mL) slowly. The ice-salt bath used was removed after that dropping. The reaction was complete (detected by LCMS and TLC) after stirred for 1 hour at room temperature. The mixture was cooled to 0° C. again and the reaction was quenched with water (1.43 mL) and 10% NaOH solution (14.3 mL) respectively. After stirred for 15 min at room temperature, the mixture was filtered and then the filter cake was washed with tetrahydrofuran (80 mL×2) and ethyl acetate EA (80 mL×2). The filtrate was dried with anhydrous sodium sulfate, filtered, and then concentrated to obtain a colorless oil product (4.535 g, 90% yield).

1.2 3-methyl-4-hydroxymethyl benzonitrile (1-2)

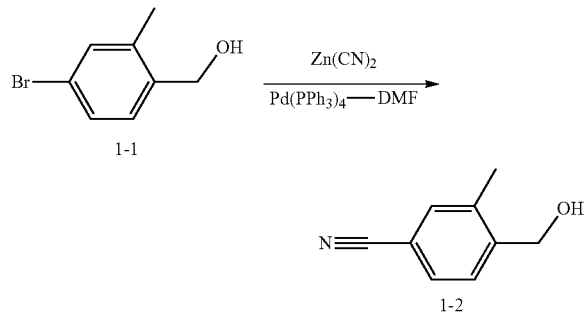

Zinc cyanide (2.63 g, 22.5 mmol) and tetrakis(triphenylphosphine) palladium (Pd(PPh$_3$)$_4$, 1.31 g, 1.13 mmol) were added into a solution of 4-bromo-2-methylbenzyl alcohol (1-1, 4.53 g, 22.5 mmol) in DMF (50 mL). After deoxygenated via argon bubbling, the reaction mixture was heated at 100° C. and reacted for 16 hours, cooled down to room temperature, diluted with ethyl acetate (120 mL), washed successively with water (120 mL×3) and saturated brine (120 mL×3), dried with anhydrous sodium sulfate and filtered. The filtrate was concentrated to obtain a crude product. The crude product was then purified by column chromatography (elution system: petroleum ether: ethyl acetate=15/1–4/1) to obtain a white solid product (2.8 g, 84% yield). The molecular ion peak shown by liquid chromatography-mass spectrometry was: MS (ESI): m/z 148.1 [M+H]$^+$. NMR: $^1$HNMR (400 MHz, CDCl3) δ: 7.57 (d, J=7.6 Hz, 1H), 7.52 (d, 7.6 Hz, 1H), 7.44 (s, 1H), 4.76 (d, J=5.6 Hz, 2H), 2.34 (s, 3H).

1.3 (Z)-3-methly-N'-hydroxy-4-hydroxymethyl benzamidine (1-3)

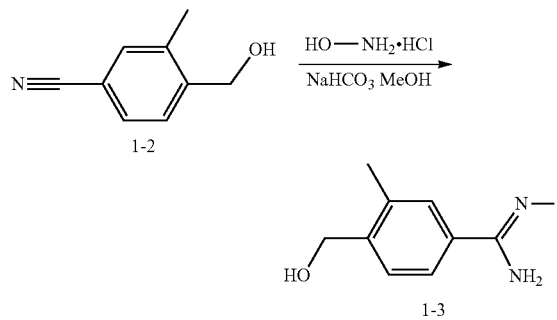

Hydroxylamine hydrochloride (2.64 g, 38 mmol) and sodium bicarbonate (6.38 g, 76 mmol) were added successively to a solution of 3-methyl-4-hydroxymethyl benzonitrile (1-2, 2.8 g, 19 mmol) in methanol (500 mL) to obtain a suspension which was then heated to reflux for 5 hours. It was then cooled to room temperature and filtered. The filter cake was washed with methanol (100 mL×2), and the obtained filtrate was concentrated to obtain 3-methyl-N'-hydroxy-4-hydroxymethyl benzamidine which was a white crude product (1-3, 3.425 g crude product, 100% yield), which was directly used in the next step. The molecular ion peak shown by liquid chromatography-mass spectrometry was: MS (ESI): m/z 181.0 [M+H]$^+$.

1.4 2-methyl-4-[5-(4-isobutylphenyl)-1,2,4-oxadiazol-3-yl]-benzyl alcohol (1-5)

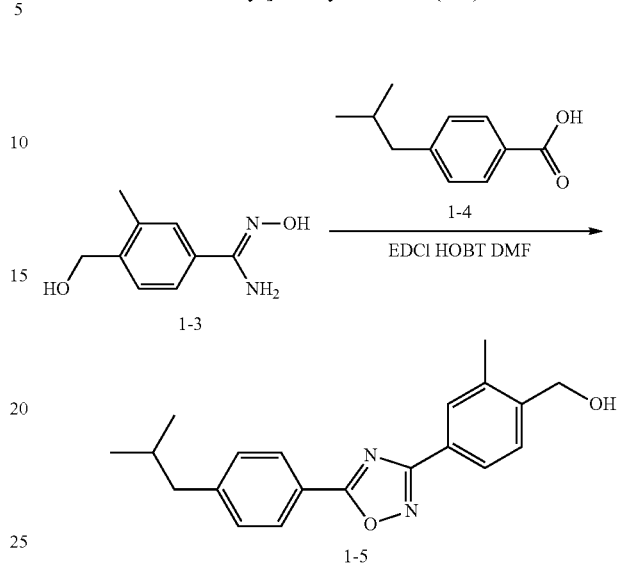

At room temperature, a solution of 4-isobutyl benzoicacid (1-4, 3.382 g, 19 mmol), 1-(3-dimethylaminopropyl)-3-ethylcarbodiimide hydrochloride (EDCI, 3.642 g, 19 mmol) and 1-hydroxybenzotrizole (2.565 g, 19 mmol) in N,N-dimethylformamide (60 mL) was stirred for 30 min before the addition of (Z)-3-methyl-N'-hydroxy-4-hydroxymethyl benzamidine (1-3, 3.42 g, 19 mmol). The mixed system was heated in 140° C. oil bath for 2 hours. LCMS indicated that starting materials reacted completely. It was then cooled to room temperature and most of N,N-dimethylformamide was removed by distillation under reduced pressure. The mixture was extracted with water and ethyl acetate, and the organic phase obtained was washed successively with 0.5N HCl solution, saturated NaHCO$_3$ solution and water, dried with anhydrous sodium sulfate and filtered, then the filtrate was concentrated to dryness. The residue was then purified by column chromatography (elution system:petroleum ether: ethyl acetate=10/1–4/1) to obtain 2-methyl-4-[5-(4-isobutylphenyl)-1,2,4-oxadiazol-3-yl]-benzyl alcohol which was a white solid product (1-5, 2.51 g, 41% yield). The molecular ion peak shown by liquid chromatography-mass spectrometry was: MS (ESI): m/z 323.0 [M+H]$^+$. NMR: $^1$HNMR (400 MHz, CDCl3) δ: 8.12 (d, J=8.4 Hz, 2H), 7.98 (m, 2H), 7.59 (d, J=8.0 Hz, 1H), 7.32 (d, J=8.4 Hz, 2H), 4.77 (s, 2H), 2.57 (d, J=7.2 Hz, 2H), 2.42 (s, 3H), 1.93 (m, 1H), 0.92 (d, J=7.2 Hz, 6H).

1.5 2-methyl-4-[5-(4-isobutylphenyl)-1,2,4-oxadiazol-3-yl]-benzaldehyde (1-6)

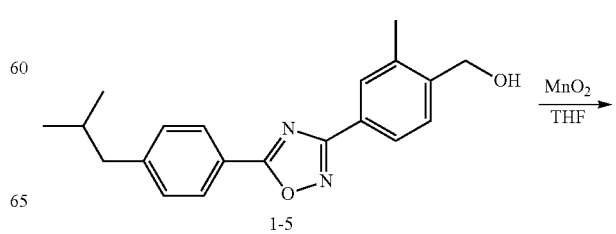

-continued

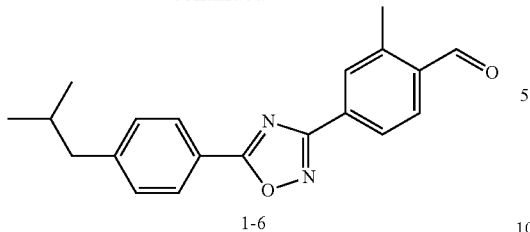

1-6

At 60° C., a suspension system of 2-methyl-4-[5-(4-isobutylphenyl)-1,2,4-oxadiazol-3-yl]-benzyl alcohol (1-5, 2.5 g, 7.76 mmol) and manganese dioxide (6.75 g, 77.6 mmol) in tetrahydrofuran (100 mL) was stirred for 2 hours. Then the suspension system was cooled to room temperature, filtered and concentrated to obtain 2-methyl-4-[5-(4-isobutylphenyl)-1,2,4-oxadiazol-3-yl]-benzaldehyde which was a white solid product (1-6, 2.4 g, 97% yield). The molecular ion peak shown by liquid chromatography-mass spectrometry was: MS (ESI): m/z 321.0 [M+H]$^+$. NMR: $^1$HNMR (400 MHz, CDCl3) δ: 10.38 (s, 1H), 8.20~8.13 (m, 4H), 7.97 (d, J=8.4 Hz, 1H), 7.37 (d, J=8.0 Hz, 2H), 2.80 (s, 3H), 2.61 (d, J=7.6 Hz, 2H), 1.96 (m, 1H), 0.96 (d, J=7.6 Hz, 6H).

1.6 1-{2-methyl-4-[5-(4-isobutylphenyl)-1,2,4-oxadiazol-3-yl]-benzyl}-3-azetidine carboxylic acid (Compound 5)

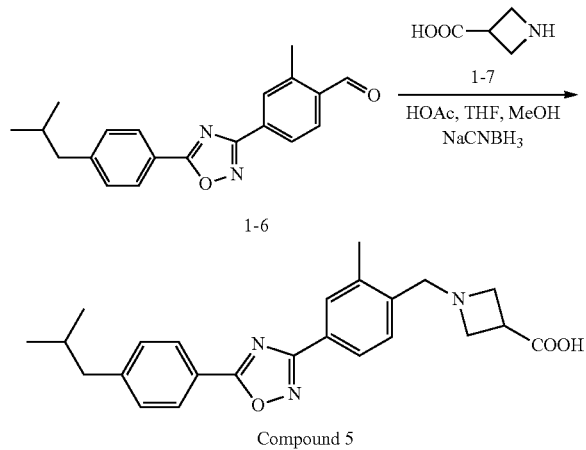

At room temperature, a solution of 2-methyl-4-[5-(4-isobutylphenyl)-1,2,4-oxadiazol-3-yl]-benzaldehyde (1-6, 0.88 g, 2.75 mmol), azetidine-3-carboxylic acid (1-7, 0.278 g, 2.75 mmol) and acetic acid (1 mL) in methanol-tetrahydrofuran (20 mL/20 mL) was stirred for 2 hours. Then a solution of sodium cyanoborohydride (1.04 g, 16.5 mmol) in methanol (60 mL) was added to the reaction mixture and the resulting mixture was stirred at room temperature for additional 16 hours and filtered. The filter cake was washed with methanol (10 mL×2) and then dried to obtain 1-{2-methyl-4-[5-(4-isobutylphenyl)-1,2,4-oxadiazol-3-yl]-benzyl}-3-azetidine carboxylic acid which was a white solid product (0.23 g, 21% yield). The molecular ion peak shown by liquid chromatography-mass spectrometry was: MS (ESI): m/z 406.0 [M+H]$^+$. NMR: $^1$HNMR (400 MHz, CD3OD) δ: 8.12 (d, J=8.0 Hz, 2H), 8.08 (s, 1H), 8.04 (d, J=7.6 Hz, 1H), 7.53 (d, J=7.6 Hz, 1H), 7.42 (d, J=8.0 Hz, 2H), 4.47 (s, 2H), 4.23 (m, 4H), 3.44 (m, 1H), 2.61 (d, J=7.2 Hz, 2H), 2.52 (s, 3H), 1.95 (m, 1H), 0.94 (d, J=7.2 Hz, 6H).

Example 6

In Vivo Pharmacokinetic Experiment of Compounds Provided by Present Invention

In this Example, the pharmacokinetic properties of compounds 1, 2, 3, 4 and 5 were evaluated via. i.v. and p.o. dosing to Sprague Dawley rats.

Experimental animals used in this Example and hereinafter were male SD rats of 7-9 weeks old, with body weight ranging from 186 to 231 g, which were purchased from Beijing Vital River Laboratory Animal Technology Co., Ltd. The animals were quarantined by veterinarian for 5 days after purchase, then animals had passed quarantine inspection were selected to be tested under SPE conditions, wherein the tested animals are assigned into 3 rats per group as follows.

Oral administration group: 2.74 mg of each of compounds 1-5 was respectively prepared into a solution of 0.3 mg/mL by using 9.113 mL 0.5% CMC-Na as a diluent. Each solution was vortexed 1-2 mins after mixed fully, and then was ultrasonically treated for 20-30 mins until a uniform suspension was obtained. The uniform suspension was used as medicine administrated to oral administration group, and the administration was conducted with a dose of 10 mL/kg body weight of each rat.

Intravenous administration group: 1.61 mg of each of compounds 1-5 was respectively prepared into a solution of 1 mg/mL by using 1.610 mL 10% HP-β-CD as a diluent. Each solution was vortexed 1-2 mins after mixed fully, and then was ultrasonically treated for 28-30 mins. The obtained solution was used as medicine administrated to intravenous administration group, and the administration was conducted with a dose of 1 mL/kg body weight of each rat.

For both oral administration group and intravenous administration group, blood samples were collected at 0.0833 h (5 min), 0.25 h (15 min), 0.5 h, 1 h, 2 h, 4 h, 8 h, and 24 h after administration. After isoflurane anesthesia 0.3 mL whole blood was collected from orbital venous plexus of the animals at each time point. The animals would be euthanized after all samples were collected.

The collected blood samples were placed in EP tubes containing heparin sodium (about 10 μl, 1000 IU/mL), which were then placed in trash ice immediately, and centrifuged at 4,000 rpm and a low temperature (4° C.) for 5 minutes. The plasma was isolated rapidly and then stored at −20° C. until analysis.

The concentration of each compound in blood was measured by LC-MS/MS-001 (Q-trap-3200) with osalmide as internal standard material, as follows. 24 μL blank plasma was added into 6 μL plasma sample (5 times of dilution), and then a solution of acetonitrile containing 150 μL internal standard material (osalmide in 100 μg/mL) was added in. The mixture was shaken for 5 minutes, and then centrifuged at 4,000 rpm for 5 minutes. 2 μL of the obtained sample was implanted into LC-MS/MS for analysis. As for undiluted plasma sample, 30 μL of it was added into a solution of acetonitrile containing 150 μL internal standard material (osalmide in 100 μg/mL). The mixture was shaken for 5 minutes, and then centrifuged at 4,000 rpm for 5 minutes. 2 μL of the obtained sample was implanted into LC-MS/MS for analysis.

As for data analysis, WinNolin (V6.2) non-compartment model (NCA) was used for calculating main metabolic pharmacokinetic parameters including t1/2, AUC(0–t), AUCinf, V, Cl, MRT, etc., and Microsoft Office EXCEL was used for calculating mean values, standard deviations and coefficients of variation.

It is clearly indicated from the data shown in Table 1 that, compared with the terminal half-life of compound 1 which was about 11 hours, the terminal half-life of each of compounds 2, 3 and 4 were less than 5.5 hours after oral administration. Therefore, the half-lives of the three compounds with halogen substituents (compounds 2, 3 and 4) were almost 50% shorten than that of compound 1.

There is a similar half-life change in the study on pharmacokinetics of intravenous administration. It is clearly indicated from the data shown in Table 2 that, compared with the terminal half-life and mean residence time (MRT) of compound 1, the terminal half-life and mean residence time of each of compounds 2, 3 and 4 substituted with halogen were reduced significantly. These data show that halogen substitutions at position 2 in compound 1 can accelerate the elimination of the compounds from the blood. What's more, the results of study on clearance (Cl) showed that, the shortening of the terminal half-life and mean residence time was not caused by the increased clearance of the compounds.

Figure 1B:
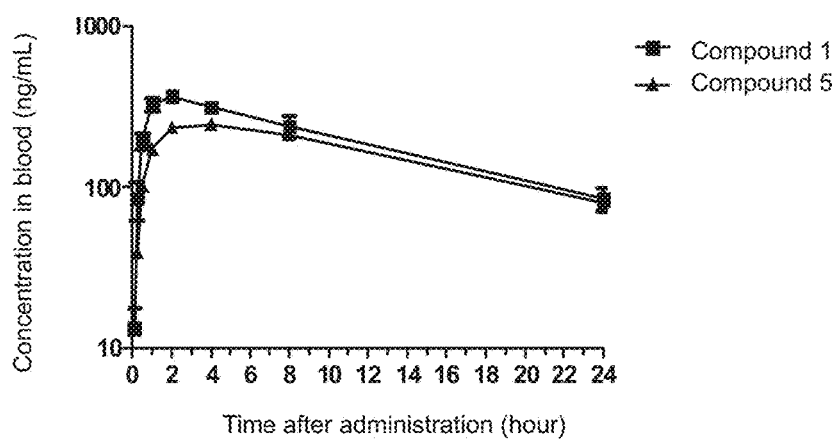

The significant shorter in vivo half-lives of compounds 2, 3 and 4 cannot be expected with conventional theory, as no similar results are obtained by substituting with other substituents at the same position of compound 1. For example, the half-life was extended rather than shortened (see Tables 1 and 2) when the substituent is methyl (corresponding to compound 5). Moreover, it can be seen from the curve of compound concentration in blood vs. time after oral administration that, compared with compounds 1 and 5, the elimination speed of compounds 2, 3 and 4 was accelerated obviously when they got to the highest concentration (FIGS. 1A and 1B).

TABLE 1 pharmacokinetics of oral administration (3 mg/kg)

| Compound | $T_{max}$ (hr) | $C_{max}$ (ng/mL) | $AUC_{inf}$ (hr * ng/mL) | T½ (hr) | F (%) |
|---|---|---|---|---|---|
| Compound 1 | 2.00 | 365 ± 51.5 | 6197 ± 147 | 10.6 ± 1.07 | 82.5 |
| Compound 2 | 2.00 | 341 ± 36.2 | 3829 ± 184 | 5.47 ± 0.63 | 63.4 |
| Compound 3 | 3.33 | 681 ± 61.1 | 8107 ± 469 | 5.30 ± 0.51 | 96.1 |
| Compound 4 | 1.15 | 346 ± 29.6 | 4419 ± 449 | 5.37 ± 0.15 | 52.9 |
| Compound 5 | 3.33 | 249 ± 8.74 | 5460 ± 401 | 12.3 ± 2.09 | 74.0 |

TABLE 2 pharmacokinetics of intravenous administration (1 mg/kg)

| Compound | CL (L/hr/kg) | Vss (L/kg) | $AUC_{inf}$ (hr * ng/mL) | T½ (hr) | $MRT_{inf}$ (hr) |
|---|---|---|---|---|---|
| Compound 1 | 0.427 ± 0.063 | 4.65 ± 0.389 | 2376 ± 329 | 8.69 ± 0.80 | 11.0 ± 1.20 |
| Compound 2 | 0.499 ± 0.039 | 3.12 ± 0.101 | 2012 ± 146 | 5.47 ± 0.42 | 6.28 ± 0.44 |
| Compound 3 | 0.366 ± 0.050 | 2.65 ± 0.229 | 2767 ± 410 | 5.04 ± 0.37 | 5.11 ± 0.39 |
| Compound 4 | 0.362 ± 0.026 | 2.75 ± 0.112 | 2768 ± 200 | 5.29 ± 0.60 | 5.23 ± 0.36 |
| Compound 5 | 0.454 ± 0.018 | 5.87 ± 0.802 | 2203 ± 89.5 | 10.1 ± 1.02 | 12.9 ± 1.24 |

Example 7

Effect of Compounds Provided by the Present Invention on the Internalization of S1P1 and S1P3

1) Internalization Effect Experiment on S1P1

It is well known that S1P1 small molecule agonists can prevent lymphocytes from entering the peripheral circulation by inducing internalization of S1P1 on cell surface. In order to determine whether the compounds provided by present invention have an activity of inducing S1P1 internalization, CHO—S cells expressing human S1P1, to replace the lymphocytes, are used as detection system of S1P1 internalization. For ease of monitoring the S1P1 on cell surface, a Myc tag is fused to N-terminal of S1P1, thus the expression of S1P1 is analyzed by flow cytometry after incubating the cells with fluorescent-labeled antibody against the Myc tag.

A 10 mM stock solution was prepared by dissolving compound 2 provided by the present invention in dimethyl sulfoxide (DMSO), and then the stock solution was diluted to different concentrations as desired with DMEM. CHO—S cells bearing human S1P1 with Myc tag were harvested and then adjusted to a density of one million cells per mL by Dulbecco's modified Eagle's medium (DMEM). Different concentrations of Compound 2 diluted in an equal volume were mixed and the cell suspension and then incubated at 37° C. for 1 hour. After incubation, the mixture was centrifuged at 800 RPM for 5 minutes to obtain the cells. The cells were resuspended in FACS buffer (PBS containing 1% BSA), and Myc antibody labelled with fluorescein isothiocyanate (FITC) (from Californian Miltenyi Biotec GmbH, USA) was added in and incubated for 1 hour on ice. The cells were washed, resuspended in pre-cooled FACS buffer and analysed by FACS Calibur flow cytometry.

The experiment data showed that compound 2 exhibited an activity of inducing S1P1 internalization in a dose-dependent manner (Table 3). Activities of compounds 3 and 4 to induce S1P1 internalization were also detected by the same method, and the results obtained show no significant difference with that of compound 1. This indicates that all the compounds obtained through substitution with F, Cl and Br (compounds 2, 3 and 4) still possess the activity of activating S1P1 while having obviously shortened half-lives.

2) Internalization Effect Experiment of S1P3

CHO—S cells expressing human S1P3 were used to perform internalization detection test. Besides cells, experimental method was the same with the method of the internalized detection experiment of S1P1.

The experiment results showed that, similar to that of compound 1, effects of compounds 2, 3 and 4 on S1P were specific, namely that the compounds only had internalization activation effect on S1P1 and had no internalization activation effect on S1P3 subtype (Table 3). This indicates that, although compounds with F, Cl or Br substituent obviously have a shortened in vivo half-live as compared with compound 1, the selectivity of the compounds to target S1P1 does not changed. In this regard, the compounds of the present invention are different from FTY720 currently used in the clinic, which is a non-selective S1P agonist. FTY720 may activate several S1P receptors, such as S1P1, S1P2, S1P3, S1P4 and S1P5, thereby resulting in a series of severe side effects, for example, bradycardia.

TABLE 3

Activity and selectivity of compounds 2, 3 and 4 to receptors

| | Receptor Internalization (EC50) | |
| --- | --- | --- |
| | S1P1 | S1P3 |
| Compound 1 | 5.69 nM | >1000 nM |
| Compound 2 | 9.83 nM | >1000 nM |
| Compound 3 | 3.21 nM | >1000 nM |
| Compound 4 | 4.20 nM | >1000 nM |

Example 8

Effect of Compounds Provided by Present Invention on the Number of Lymphocytes in the Peripheral Blood S1P1, which is expressed on the surface of lymphocytes, is essential for lymphocytes to leave the secondary lymphoid tissue and then enter into the peripheral circulation. Small molecule agonists of S1P1 can activate the receptor and result in an internalization effect on the receptor. This mechanism is a currently known mechanism by which lymphocytes are prevented from leaving the secondary lymphoid tissue, then resulting in an decreased number of lymphocytes in the peripheral circulation. In order to determine whether the compounds provided by present invention can reduce the number of lymphocytes in the peripheral blood, an in vivo effect experiment on lymphocytes is performed.

An appropriate amount of compound 2 was prepared as a suspension with sodium carboxymethylcellulose (CMC-Na) and was given orally to three Sprague-Dawley (SD) rats. Blood samples (0.5 ml) were collected at 30 min before the administration and at different time points after the administration (the collected blood samples were placed in EP tubes containing an appropriate amount of EDTA-2K solution), and analyzed on ADVIA2120 blood cell analyzer directly.

Figure 2:
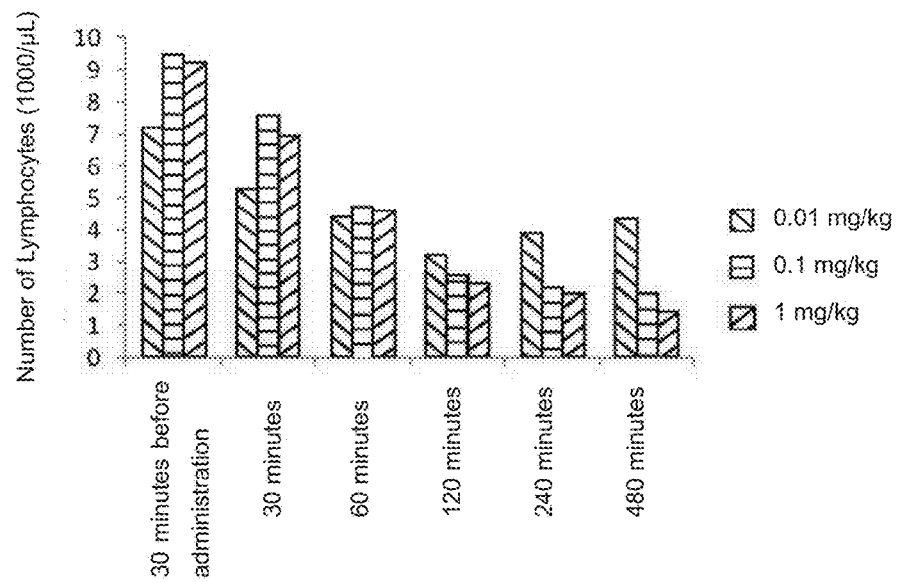
FIG. 2 shows experimental results of Example 8, which showed the number of lymphocytes in the peripheral blood was reduced by compound 2 of the present invention.

The experiment results showed that compound 2 reduced the number of lymphocytes in the peripheral blood effectively. The number of lymphocytes in the peripheral blood was reduced obviously at 30 minutes after the administration, and further reduced at all sampling time points (30, 120, 240, 360 and 480 minutes). Compound 2, in all the three doses evaluated, had the activity, wherein more than 50% reduction of lymphocytes in the peripheral blood were observed only with a dose of 0.01 mg/kg, and the most reduction were observed with a dose of 1 mg/kg (FIG. 2).

What's more, the effect of compound 2 is specific to lymphocytes, and compound 2 changed the number of peripheral mononuclear cells and other leukocytes unobviously.

Figure 3:
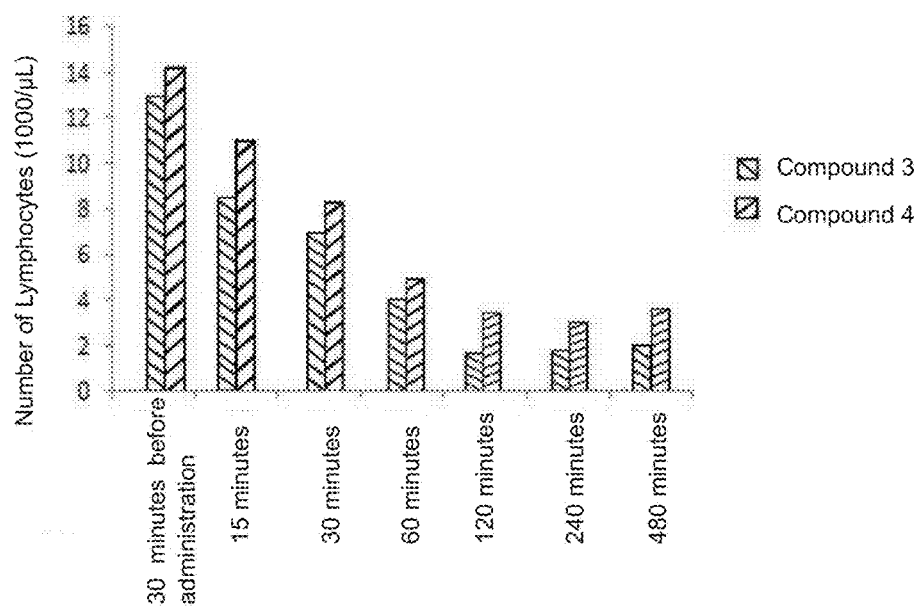
FIG. 3 shows experimental results of Example 8, which showed the number of lymphocytes in the peripheral blood was reduced by compounds 3 and 4 of the present invention, wherein compounds 3 and 4 were administered at 0.1 mg/kg body weight into rats.
Figure 4:
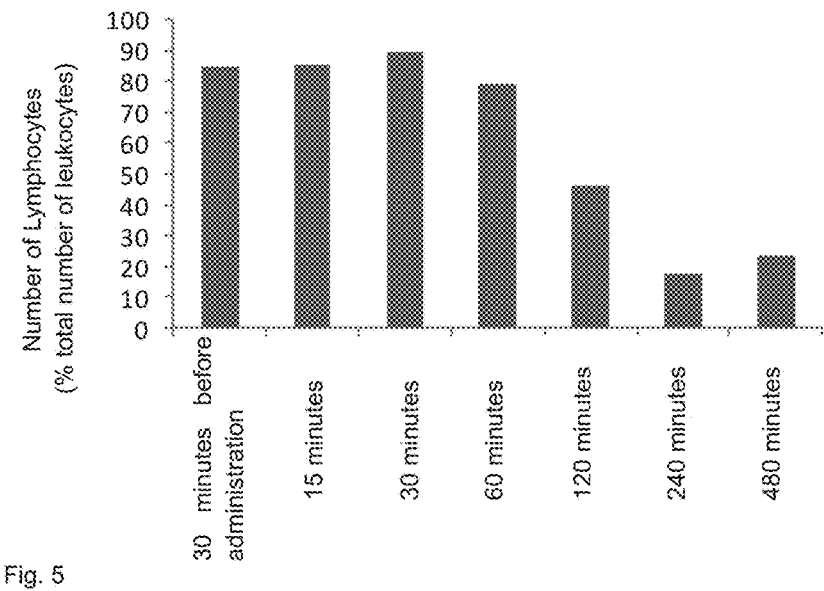
FIG. 4 shows experimental results of Example 8, which showed the number of lymphocytes in the peripheral blood was reduced by compound 5 of the present invention, wherein compound 5 was administered at 0.1 mg/kg body weight into rats.

It was found that effect of compounds 3, 4 and 5 on lymphocytes was similar to that of compound 2 by testing compounds 3, 4 and 5 of the present invention with the same method (FIG. 3 and FIG. 4).

Example 9

Effect of Compound 2 on the Development of Collagen Type II-Induced Arthritis in Lewis Rats Rheumatoid arthritis in human is an autoimmune disease, in which the patient' own immune system attacks joint tissues. Lymphocytes including T and B cells play an important part in the pathogenesis of the disease. It is known that inhibition of T cell functions by blocking the activation of T cells is an effective treatment of rheumatoid arthritis. Since Compound 2 blocks egress of lymphocytes, it was of interest to determine if it would be efficacious in inhibiting the development of arthritis in the rat CIA mode. To perform the testing, Lewis rats were induced to develop the disease as follows. Rats were anesthetized with isoflurane and were injected intradermally with a total of 0.5 mL CII/CFA emulsion. The emulsion was injected at 3 sites, one site at the base of the tail (0.1 mL), and the other two sites (0.2 mL/site) on the back of the rat near to the base of the tail. An identical booster injection was given i.d. at 7 days after the primary immunization avoiding previous injection sites.

Figure 5:
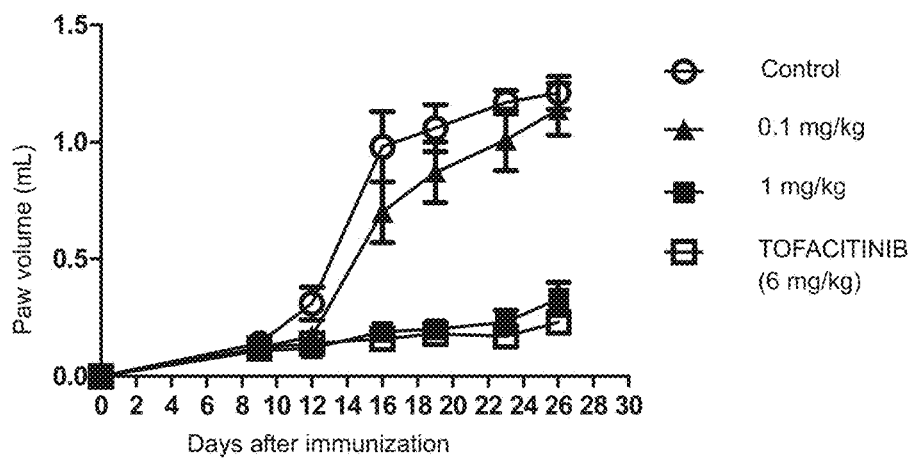
FIG. 5 shows experimental results of Example 9, which showed the development of arthroncus in arthritis was inhibited by compound 2 provided by present invention.
Figure 6:
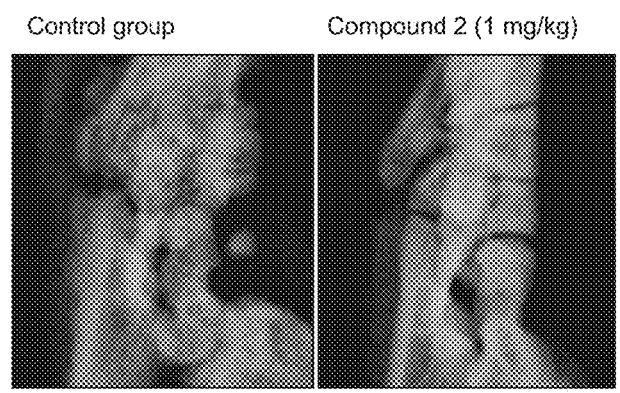
FIG. 6 shows experimental results of Example 9, which showed the damage of joint structure in arthritis was inhibited by compound 2 provided by present invention.

Compound 2 was prepared as a suspension in 0.5% CMC-Na and was given orally to the rats at the time of CII/CFA injection. The positive control group was given TOFACITINIB orally on day 12 after sensitization. The severity of arthritis in four paws was scored 2 times per week starting on day 7 after sensitization. The criteria was as follows: score 0: No evidence of erythema and swelling; score 1: Erythema and mild swelling confined to the mid-foot (tarsals) or ankle joint; score 2: Erythema and mild swelling extending from the ankle to the mid-foot; score 3: Erythema and moderate swelling extending from the ankle to the metatarsal joints; score 4: Erythema and severe swelling encompass the ankle, foot, and digits. Joint swelling, measured by the volume of hind paws using Plethysmometer, was determined on Day 0, and then 2 times per week from Day 7 to Day 28. Destruction of the joint was determined by X-Ray examination on Day 28. The results showed that at 1 mg/kg, Compound 2 was effective in inhibiting the development of arthritis based on joint swelling (FIG. 5) and destruction of joint structure (FIG. 6). It can be seen from FIG. 5 that Compound 2 had a similar function with TOFACITINIB, but the dosage of it was decreased significantly.

Example 10

Effect of Compound 2 on the Development of Experimental Autoimmune Encephalitis (EAE)

S1P1 agonists have been shown to be effective in human multiple sclerosis and in animal model of MS. Compound 2 was evaluated for its efficacy for experimental autoimmune encephalomyelitis (EAE), a mouse model of human multiple sclerosis. Eighty female C57BL/6 mice were randomly assigned into eight groups based on body weight and immunized in this study. Each group consisted of ten (10) mice.

To induce the disease, MOG 35-55 (MOG, myelin oligodendrocyte glycoprotein) was dissolved in saline to a concentration of 2 mg/mL, and was emulsified in modified complete Freund's Adjuvant (CFA). Mice were anesthetized with isoflurane and were then injected with 100 μL of emulsion subcutaneously into the shaved backs of the mice at three sites, one along the midline of the back between the shoulders, and two on each side of the midline on the lower back. Pertuxus toxin (200 ng in 200 μL of PBS) was administered i.p. on the day of immunization and 48 hours after for all groups. EAE development was assessed by clinically scoring of the mice once daily from Day 0 to Day 30 post immunization.

Figure 7:
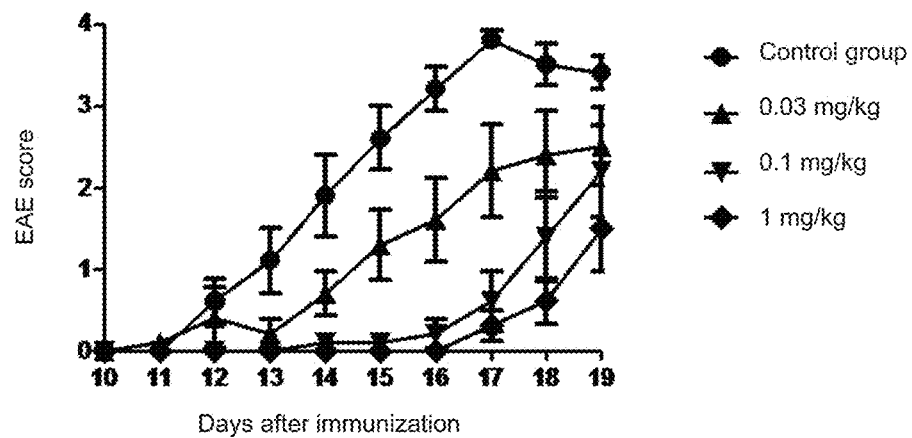
FIG. 7 shows experimental results of Example 10, which showed the development of EAE was inhibited by compound 2 provided by present invention.

Compound 2 prepared as a Na CMC suspension, was administered orally starting at the time of MOG immunization and continued for the entire duration of the study. The data showed that at all three dosages evaluated (0.03, 0.1 and 1 mg/kg), Compound 2 effectively inhibited development of EAE (FIG. 7).

Example 11

Effect of Compound 2 on the Cardiovascular Function of Beagle Dogs

FTY720 is a non-selective S1P1 agonist that has been shown to have various cardiovascular effects including bradycardia in humans. To determine whether Compound 2 has an effect on heart rate and QT interval, the compound was evaluated in a telemetry assay in conscious beagle dog.

An appropriate amount of CMC-Na was prepared as a 0.5% CMC-Na (w/v) solution with sterilized water for injection. The solution was prepared one day before administration.

Solutions of Compound 2 (samples) with the concentration of 2, 6 and 20 mg/mL were prepared one day before administration as follows. An appropriate amount of Compound 2 was added into an appropriate amount of 0.5% CMC-Na solution. The obtained mixture was emulsified and homogenized on an emulsification isotropic machine. Theoretical concentrations of Compound 2 in the prepared sample solutions were 2, 6 and 20 mg/mL.

A total of 8 animals and a Double Latin squared experimental design were used in this experiment. Administration cycles were separated by 3-5 days. One day before each administration cycle, the animals were weighted and fasted overnight. On the day of administration, telemetry system (Implantable physiological signal telemetry system 1, Data Science International Inc., USA) was turned on, test parameters were set, implants were activated and physiological indexes of the animals were recorded. About two hours later after the turning on of the system, the animals were administered according to the cycles designed. Index data of blood pressure, electrocardiogram, body temperature and the like of the animals were collected within 24 hours after the administration. During the collection, the system was turned off properly and then turned on again in order to avoid possible data overflow. The switching process did not affect the value of the setting data points and times switching the system were recorded. On the next day when the recording was completed, the telemetry system was turned off. Time points of detection are: 1 hour before administration (−1 h), and 0.5 h (±5 min), 1 h (±10 min), 1.5 h (±10 min), 2 h (±15 min), 3 h (±15 min), 4 h (±15 min), 8 h (±45 min), 24 h (±1 h) after administration. All data was collected by PONEMAH Version 4.8 software automatically. Parameters would be analyzed using artificial set after the collection was completed. The data was, firstly, analyzed by PONEMAH Version 4.8 software automatically, and then checked point by point artificially for selected values. As for indexes of heart rate, blood pressure, respiration and body temperature, mean values of continuous waveform within 1 min were selected, and mean values of continuous waveform within 10 seconds were selected for other electro-cardio indexes. During the value selection, immediate data at the detection time points was preferred. However, if there were problems such as large noise disturbance, abnormalities in heart rate, or no clearly waveform could be identified at the detection time points, waveform with clear signal in the given range was selected. Furthermore, if there still no clear waveform at the given range was available for analysis, data which is available for analysis should be found around the value points, which should be explained specially in a value point table. Time at which values were selected were recorded.

Statistical software SPSS13.0 was used to process data in this experiment. Two-tailed analyses were performed whereby the level of significance was set at p<0.05. Indexes of blood pressure, electrocardiogram, respiration and body temperature were expressed as "mean±standard error", and then analyzed according to following procedure: firstly, homogeneity test was performed on the data by use of Levene Test, and if the data was uniform (P≤0.05), single-factor variance analysis was performed; and if the result of variance analysis was significant (P≤0.05), Dunnett's multiple comparison was performed on difference between vehicle group and sample group. If the result of Levene Test was significant (P≤0.05), Kruskal-wallis non-parametric test was performed; and if the result of Kruskal-wallis non-parametric test was significant (P≤0.05), pairwise comparison was performed by use of Mann-Whitney U test.

The change range was calculated after the data collected at time points with significant difference or significant change trend are normalized. The formulae of normalization was Δ %=[(b1−b0)−(a1−a0)]/a1×100, wherein b1 represented value of time point after administrating the samples, b0 represented value of time point before administrating the samples, a1 represented corresponding value of time point after administrating the vehicle, a0 represented value of time point before administrating the vehicle, and Δ % represented the change range.

Figure 8A:
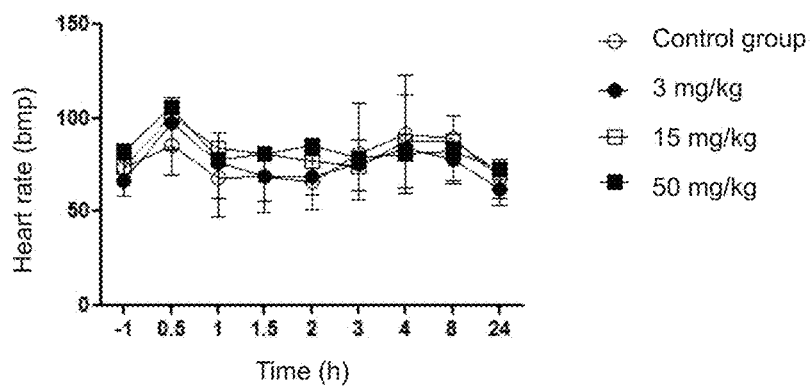
FIGS. 8A to 8C show experimental results of Example 11, which showed the effect of compound 2 provided by present invention on electrocardiographic index.
Figure 8B:
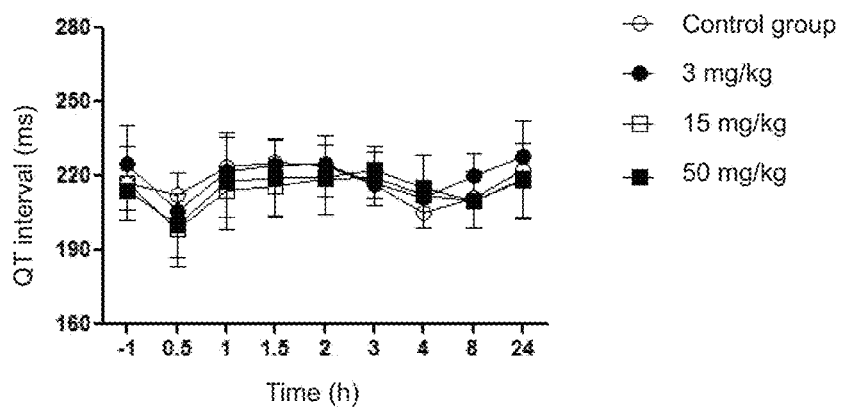
Figure 8C:
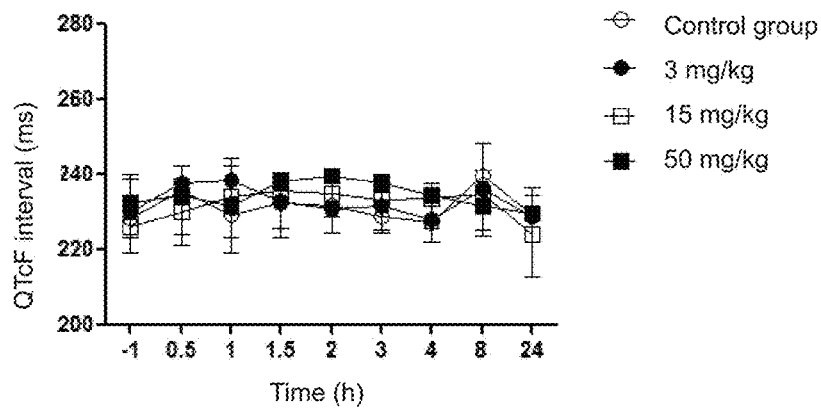

Comparing heart rate, QT interval and QTcF interval of animals administrated with doses of sample to indexes of electrocardiogram of animals administrated with vehicle, no significant difference (P>0.05) or change trend was found (FIG. 8A to FIG. 8C).

As for synthesis method of 1-{2-fluoro-4-[5-(4-isobutyl-phenyl)-1,2,4-oxadiazol-3-yl]-benzyl}-3-azetidine carboxylic acid (Compound 2), Examples of optimizing the method and the condition thereof are provided below.

The synthesis of compound 2 will be carried out according to the method including the following steps:

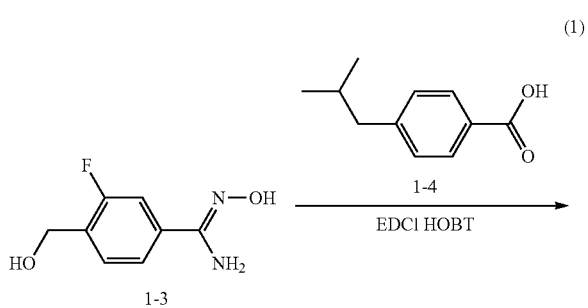

(1)

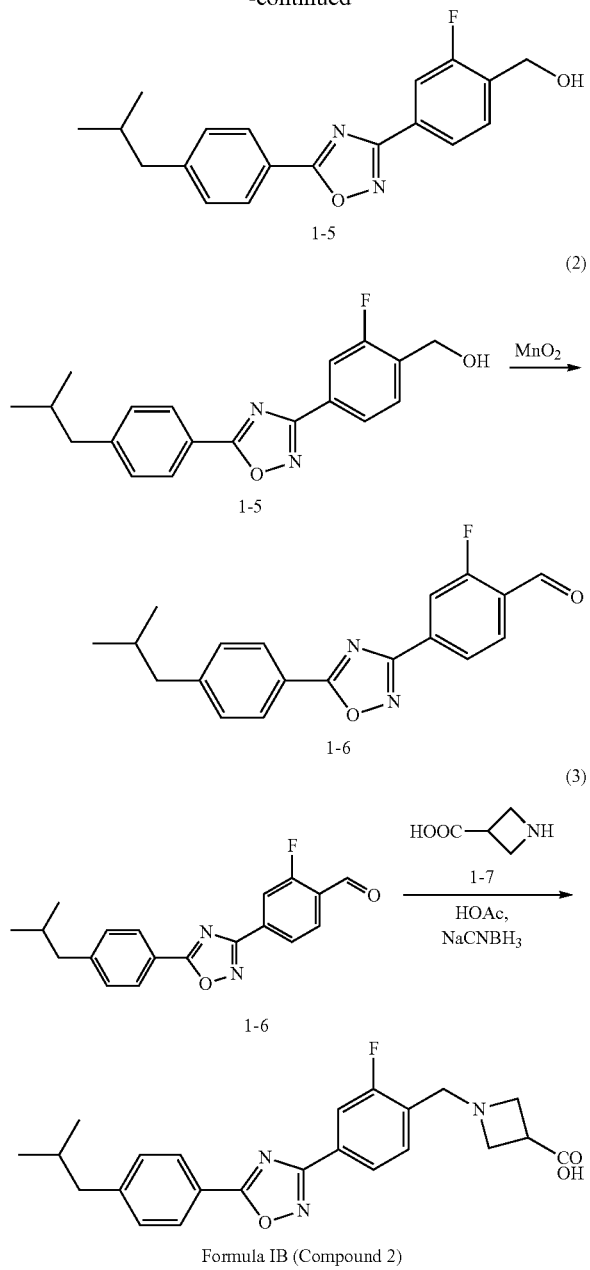

Firstly, the above crystallization operation was performed according to contents listed in Table 4 for screening the preferred crystallization solvent.

TABLE 4

Screening of solvents and the amount thereof for crystallization purification

| Solvent | Amount of the solvent (crude product:solvent) | Purity of crude product | Purity of pure product | Yield of purification |
|---|---|---|---|---|
| Ethyl acetate | 1 g:1 ml | 77.25% | 96.72% | A little of precipitates |
| Acetone | 1 g:1 ml | 77.25% | 95.22% | A little of precipitates |
| Methanol | 1 g:3 ml | 77.25% | 99.08% | 55.4% |
| Ethanol | 1 g:3 ml | 77.25% | 99.36% | 37.4% |
| Tetrahydrofuran | 1 g:1 ml | 77.25% | | Clear solution |
| Dichloromethane | 1 g:1 ml | 77.25% | 98.58% | A little of precipitates |
| Water | 1 g:1 ml | 77.25% | 95.34% | 84% |

It can be seen from Table 4 that, when single solvent was used for crystallization, the purity of the product was increased obviously by using methanol or ethanol as solvent. The yield was much higher when using methanol than using ethanol, but it was only 55.4%. The purity of the product was not increased substantially by using water as solvent, but the yield loss was minor. Therefore, it had been tried in the follow-up study to use a mixed solvent of methanol and water as crystallization solvent.

Secondly, the above crystallization operation was performed according to contents listed in Table 5 for screening the preferred ratio of methanol and water in the mixed solvent. The ratio of the crude product (in g, by weight) to the mixed solvent (in ml, by volume) for crystallization is 1:5.

TABLE 5

Screening of the ratio of methanol and water in the mixed solvent

| Solvent | Solvent ratio (volume ratio) | Purity of crude product | Purity of pure product | Yield of purification |
|---|---|---|---|---|
| Methanol and water | 1:1 | 77.25% | 98.32% | 75.2% |
| Methanol and water | 2:1 | 77.25% | 99.13% | 73.1% |
| Methanol and water | 3:1 | 77.25% | 99.27% | 72.7% |
| Methanol and water | 1:2 | 77.25% | 97.20% | 79.8% |
| Methanol and water | 1:3 | 77.25% | 95.68% | 83.2% |

It can be seen from Table 5 that the purity of the product was increased, but the yield was decreased by increasing the amount of methanol in the mixed solvent; and the yield of purification was increased, but the purity of the product was decreased by increasing the amount of water. Overall considered, a volume ratio of 3:1 was selected as the ratio of methanol and water in the mixed solvent.

Thirdly, the above crystallization operation was performed according to contents listed in Table 6 for screening the preferred amount of the mixed solvent. The volume ratio of methanol and water in the mixed solvent is 3:1.

Example 12

Screening for Step (1) in Synthesis Method of the Present Invention

Crude product of compound represented by formula 1-5 was prepared and characterized according to Example 2. The purity detected by LCMS was 77.25%. A screening for crystallization purification condition was conducted on the prepared crude product. Crystallization operation was as follows: the crude product was dissolved in a crystallization solvent, crystallized at 20° C., and dried by vacuum to obtain 2-fluoro-4-[5-(4-isobutylphenyl)-1,2,4-oxadiazol-3-yl]-benzyl alcohol represented by formula 1-5 which is an almost white solid product. The purity was detected by LCMS.

TABLE 6

Screening of the amount of the solvent

| Solvent | Amount of solvent (crude product: solvent) | Purity of crude product | Purity of pure product | Yield of purification |
|---|---|---|---|---|
| Methanol and water | 1 g:3 ml | 77.25% | 98.99% | 69.9% |
| Methanol and water | 1 g:5 ml | 77.25% | 99.16% | 72.2% |
| Methanol and water | 1 g:10 ml | 77.25% | 99.05% | 68.9% |
| Methanol and water | 1 g:20 ml | 77.25% | 99.30% | 67.2% |

It can be seen from Table 6 that a high yield and purity were obtained when the ratio of weight of the crude product to volume of the solvent was 1 g:5 mL. However, although a higher purity was obtained when the ratio of weight of the crude product to volume of the solvent is 1 g:20 mL than the ratio is 1 g:5 mL, yield was less. Therefore, a ratio of 1 g:5 mL was selected as the ratio of weight of the crude product to volume of the solvent used as the solvent system for crystallization.

Example 13

Screening for Step (2) in Synthesis Method of the Present Invention

Step (2) of the present invention was conducted according to the following procedure: 2-fluoro-4-[5-(4-isobutylphenyl)-1,2,4-oxadiazol-3-yl]-benzyl alcohol represented by formula 1-5 purified from Example 1 was dissolved in reaction solvent, and then active manganese dioxide was added in. The reaction liquid was heated to reflux and continued to react. The reaction was cooled down to room temperature and filtered. A light yellow filtrate was collected, dried with anhydrous sodium sulfate and concentrated under reduced pressure to obtain 2-fluoro-4-[5-(4-isobutylphenyl)-1,2,4-oxadiazol-3-yl]-benzaldehyde represented by formula 1-6 which was a white solid product. The conversion rate was detected by LCMS.

Firstly, the synthesis step above was carried out according to contents listed in Table 7 for screening the preferred reaction solvent. The mole ratio of 2-fluoro-4-[5-(4-isobutylphenyl)-1,2,4-oxadiazol-3-yl]-benzyl alcohol represented by formula 1-5 to manganese dioxide was 1:6. Expression "raw material" in Tables 7-9 refers to 2-fluoro-4-[5-(4-isobutylphenyl)-1,2,4-oxadiazol-3-yl]-benzyl alcohol represented by formula 1-5.

TABLE 7

Screening of the reaction solvent

| Solvent | Amount of solvent (raw material:solvent) | Reaction time | Conversion rate (LCMS) | Yield |
|---|---|---|---|---|
| Tetrahydrofuran | 1 g:10 ml | 1 h | 96.26% | 92.2% |
| Ethyl acetate | 1 g:10 ml | 1 h | 93.3% | 93.3% |
| Toluene | 1 g:10 ml | 1 h | 91.7% | 91.7% |

It can be seen from Table 7 that there was a little effect on the conversion rate and the yield when tetrahydrofuran, ethyl acetate or toluene was used as the reaction solvent. However, a safety risk existed when tetrahydrofuran was used as the reaction solvent and a high toxicity when toluene was used as the reaction solvent, thus, ethyl acetate was selected as the reaction solvent.

Secondly, the synthesis step above was carried out according to contents listed in Table 8 for screening the preferred amount of the solvent. Ethyl acetate was used as the reaction solvent, and the mole ratio of 2-fluoro-4-[5-(4-isobutylphenyl)-1,2,4-oxadiazol-3-yl]-benzyl alcohol represented by formula 1-5 to manganese dioxide is 1:6.

TABLE 8

Screening of the amount of the reaction solvent

| Amount of the solvent (raw material:solvent) | Reaction time | Conversion rate (LCMS) | Yield |
|---|---|---|---|
| 1 g:10 ml | 1 h | 97.76% | 93.3% |
| 1 g:20 ml | 1 h | 98.93% | 92.6% |
| 1 g:30 ml | 1 h | 98.83% | 93.1% |

It can be seen from Table 8 that there was a little effect on the conversion rate and the yield when the ratio of weight of the raw material to the volume of the solvent was 1 g:10 ml, 1 g:20 ml and 1 g:30 ml. Considering cost, the ratio of 1 g:10 ml was selected as the amount of the reaction solvent.

Thirdly, the synthesis step above was carried out according to contents listed in Table 9 for screening the preferred amount of manganese dioxide. An amount of 1 g:10 ml of 2-fluoro-4-[5-(4-isobutylphenyl)-1,2,4-oxadiazol-3-yl]-benzyl alcohol represented by formula 1-5 to ethyl acetate was used.

TABLE 9

Screening of the amount of oxidant

| Amount of oxidant (the mole ratio of raw material to manganese dioxide) | Reaction time | Conversion rate (LCMS) | Yield |
|---|---|---|---|
| 1:4 | 3 h | 96.91% | 86.6% |
| 1:5 | 3 h | 97.06% | 91.0% |
| 1:6 | 3 h | 97.03% | 93.3% |
| 1:10 | 3 h | 97.12% | 93.6% |

It can be seen from Table 9 that a high conversion rate and yield were obtained when the mole ratio of raw material to manganese dioxide was 1:6. However, there was a little effect on conversion rate and yield when the mole ratio of raw material to manganese dioxide was increased to 1:10. Therefore, considering both cost and yield, a mole ratio of 1:6 was selected as the amount of raw material and manganese dioxide.

Example 14

Screening for Step (3) in Synthesis Methods of the Present Invention

The step (3) of the present invention was conducted according to the following procedure:

At room temperature, 2-fluoro-4-[5-(4-isobutylphenyl)-1,2,4-oxadiazol-3-yl]-benzaldehyde of formula 1-6, azetidine-3-carboxylic acid of formula 1-7 and glacial acetic acid were added into the reaction solvent and stirred for 2 hours at 20° C. NaBH3CN was dissolved in methanol, and then the solution of NaBH3CN in methanol was added dropwise into the reaction system within 1 hour. The reaction liquid was stirred to react at 20° C. after dropping and filtered. The filter cake was washed with methanol and then dried to obtain 1-{2-fluoro-4-[5-(4-isobutylphenyl)-1,2,4-oxadiazol-3-yl]-benzyl}-3-azetidine carboxylic acid represented by formula IB (compound 2) which was a white solid product. The conversion rate was detected by LCMS.

Firstly, the synthesis step above was carried out according to contents listed in Table 10 for screening the preferred reaction solvent. The mole ratio of 2-fluoro-4-[5-(4-isobutylphenyl)-1,2,4-oxadiazol-3-yl]-benzaldehyde of formula 1-6 to azetidine-3-carboxylic acid of formula 1-7 was 1:1.05; the mole ratio of 2-fluoro-4-[5-(4-isobutylphenyl)-1,2,4-oxadiazol-3-yl]-benzaldehyde of formula 1-6 to sodium cyanoborohydride is 1:1; the dropping temperature of the solution of NaBH3CN in methanol was 15-20° C.; and expression "raw material" in Tables 10-12 referred to 2-fluoro-4-[5-(4-isobutylphenyl)-1,2,4-oxadiazol-3-yl]-benzaldehyde represented by formula 1-6.

TABLE 10

Screening of the reaction solvent

| Solvent | Amount of solvent (raw material:solvent) | Reaction time | Conversion rate (LCMS) | Yield |
|---|---|---|---|---|
| Tetrahydrofuran | 1 g:40 ml | 6 h | 1.64% | |
| Methanol | 1 g:40 ml | 6 h | 79.26% | 69.10% |
| Ethanol | 1 g:40 ml | 6 h | 66.20% | 53.23% |

It can be seen from Table 10 that the conversion rate was very low when tetrahydrofuran was used as the reaction solvent. Whereas both the conversion rate and the yield were higher when methanol or ethanol was used as the reaction solvent.

Secondly, the synthesis step above was carried out according to contents listed in Table 11 for screening the preferred amount of reducing agent. The mole ratio of 2-fluoro-4-[5-(4-isobutylphenyl)-1,2,4-oxadiazol-3-yl]-benzaldehyde of formula 1-6 to azetidine-3-carboxylic acid of formula 1-7 was 1:1.05; the reaction solvent was methanol and the dropping temperature of the solution of NaBH3CN in methanol was 15-20° C.

TABLE 11

Screening of the amount of reducing agent

| Amount of reducing agent (the mole ratio of raw material to sodium cyanoborohydride) | Reaction time | Conversion rate (LCMS) | Yield | Purity |
|---|---|---|---|---|
| 1:0.5 | 15 h | 66.42% | 67.20% | 94.58% |
| 1:1 | 15 h | 79.26% | 69.10% | 95.50% |
| 1:2 | 15 h | 73.77% | 65.61% | 94.24% |
| 1:6 | 15 h | 64.51% | 53.27% | 94.36% |

It can be seen from Table 11 that the conversion rate, the yield and the purity of the product were all higher when the mole ratio of raw material to sodium cyanoborohydride was 1:1.

Thirdly, the synthesis step above was carried out according to contents listed in Table 12 for screening the preferred dropping temperature of the reducing agent. The mole ratio of 2-fluoro-4-[5-(4-isobutylphenyl)-1,2,4-oxadiazol-3-yl]-benzaldehyde of formula 1-6 to azetidine-3-carboxylic acid of formula 1-7 was 1:1.05; and the reaction solvent was methanol.

TABLE 12

Screening of dropping temperature of the reducing agent

| Temperature | Amount of reducing agent (raw material (1-6): reducing agent) | Amount of solvent (raw material:solvent) | Dropping time | Conversion rate | Purity |
|---|---|---|---|---|---|
| 0-5° C. | 1 Eq. | 40 V | 20 min | 67.65% | 95.61% |
| 5-15° C. | 1 Eq. | 40 V | 20 min | 71.04% | 96.91% |
| 15-20° C. | 1 Eq. | 40 V | 20 min | 74.50% | 97.91% |

It can be seen from Table 12 that both the conversion rate and the purity of the product were higher when the dropping temperature of sodium cyanoborohydride was 15-20° C.

Example 15

Synthesis Method of the Present Invention (1) At room temperature, 4-isobutyl benzoicacid (1-4, 0.148 Kg, 0.83 mol) was dissolved in N,N-dimethylformamide (1.7 L), and then 1-hydroxybenzotrizole (0.11 Kg, 0.83 mol) and 1-(3-dimethylaminopropyl)-3-ethylcarbodiimide hydrochloride (0.16 Kg, 0.83 mol) were added in. The reaction liquid was heated to 30° C. and stirred for 30 min, then 3-fluoro-N'-hydroxy-4-hydroxymethyl benzamidine (1-3, 0.153 Kg, 0.83 mol) was added to the reaction liquid. The reaction liquid was heated to 140° C. and reacted for 2 hours, cooled down to room temperature, and the N,N-dimethylformamide was removed by concentration under reduced pressure. The concentrate was dissolved in ethyl acetate (2.0 L), and washed successively with water (1.5 L×2) and saturated NaHCO3 solution (1.5 L). The organic phase was collected and dried with anhydrous sodium sulfate, and concentrated under reduced pressure to obtain 256 g crude product.

The crude product obtained from above was recrystallized by 1.28 L mixed solvent of methanol and water (a volume ratio of 3:1), crystallized at 20° C., filtered and dried in vacuum to obtain 2-fluoro-4-[5-(4-isobutylphenyl)-1,2,4-oxadiazol-3-yl]-benzyl alcohol which was an almost white solid product (1-5, 182 g, 71% yield). The purity detected by LCMS was 93.1%.

MS (ESI): m/z 327.0 [M+H]$^+$. NMR: $^1$HNMR (400 MHz, CDCl3) δ: 8.11 (d, J=8.0 Hz, 2H), 7.98 (m, 1H), 7.86 (m, 1H), 7.59 (t, J=8.0 Hz, 7.6 Hz, 1H), 7.33 (d, J=8.0 Hz, 2H), 4.85 (s, 2H), 2.57 (d, J=6.8 Hz, 2H), 1.93 (m, 1H), 0.93 (d, J=6.8 Hz, 6H).

(2) At room temperature, 2-fluoro-4-[5-(4-isobutylphenyl)-1,2,4-oxadiazol-3-yl]-benzyl alcohol (1-5, 0.14 Kg, 0.43 mol) was dissolved in ethyl acetate (1.4 L), and then active manganese dioxide (0.21 Kg, 2.42 mol) was added in. The reaction liquid was heated to reflux and reacted for 3 hours, cooled to room temperature and filtered. A light yellow filtrate was collected, dried with anhydrous sodium sulfate and concentrated under reduced pressure to obtain 2-fluoro-4-[5-(4-isobutylphenyl)-1,2,4-oxadiazol-3-yl]-benzaldehyde which was a white solid product (1-6, 139 g, 99.0% yield). The purity detected by LCMS was 97.6%.

MS (ESI): m/z 325.0 [M+H]$^+$. NMR: $^1$HNMR (400 MHz, CDCl3) δ: 10.42 (s, 1H), 8.12~7.99 (m, 5H), 7.34 (d, J=7.2 Hz, 2H), 2.58 (d, J=6.4 Hz, 2H), 1.93 (m, 1H), 0.93 (d, J=6.4 Hz, 6H).

(3) At room temperature, 2-fluoro-4-[5-(4-isobutylphenyl)-1,2,4-oxadiazol-3-yl]-benzaldehyde (1-6, 60 g, 0.185 mol), azetidine-3-carboxylic acid (1-7, 19.5 g, 0.193 mol) and glacial acetic acid (360 mL, 0.63 mol) were added into methanol (1.6 L) and stirred for 2 hours at 20° C. NaBH3CN (11.5 g, 0.185 mol) was dissolved in methanol (200 mL), and then the solution of NaBH3CN in methanol was added dropwise into the reaction system within 1 hour. The dropping temperature was controlled at 15-20° C. The reaction liquid was stirred for 16 hours at 20° C. after dropping and filtered. The filter cake was washed with 300 mL methanol and then dried to obtain 1-{2-fluoro-4-[5-(4-isobutylphenyl)-1,2,4-oxadiazol-3-yl]-benzyl}-3-azetidine carboxylic acid which was a white solid product (compound 2, 67 g, 89.0% yield). The purity detected by LCMS was 98.8%.

MS (ESI): m/z 410.2 [M+H]$^+$. NMR: $^1$HNMR (400 MHz, CDCl3) δ: 8.13 (d, J=8.4 Hz, 2H), 8.05 (m, 1H), 7.97 (m, 1H), 7.68 (t, J=8.0 Hz, 7.6 Hz, 1H), 7.42 (d, J=8.4 Hz, 2H), 4.40 (s, 2H), 4.15 (m, 4H), 3.41 (m, 1H), 2.61 (d, J=7.2 Hz, 2H), 1.95 (m, 1H), 0.94 (d, J=7.2 Hz, 6H).

Example 16

Synthesis Method of the Present Invention (1) At room temperature, 4-isobutyl benzoicacid (1-4, 1.477 Kg, 8.30 mol) was dissolved in N,N-dimethylformamide (17 L), and then 1-hydroxybenzotrizole (1.12 Kg, 8.30 mol) and 1-(3-dimethylaminopropyl)-3-ethylcarbodiimide hydrochloride (1.58 Kg, 8.30 mol) were added in. The reaction liquid was heated to 30° C. and stirred for 30 min, then 3-fluoro-N'-hydroxy-4-hydroxymethyl benzamidine (1-3, 1.527 Kg, 8.30 mol) was added to the reaction liquid. The reaction liquid was heated to 140° C. and reacted for 2 hours, cooled down to room temperature, and the N,N-dimethylformamide was removed by concentration under reduced pressure. The concentrate was dissolved in ethyl acetate (20 L), and washed successively with water (15 L×2) and saturated NaHCO3 solution (15 L). The organic phase was collected and dried with anhydrous sodium sulfate, and concentrated under reduced pressure to obtain 2.6 Kg crude product.

The crude product obtained from above was recrystallized by 12.5 L mixed solvent of methanol and water (a volume ratio of 3:1), crystallized at 20° C., filtered and dried in vacuum to obtain 2-fluoro-4-[5-(4-isobutylphenyl)-1,2,4-oxadiazol-3-yl]-benzyl alcohol which was an almost white solid product (1-5, 1.9 Kg, 73% yield). The purity detected by LCMS was 93.89%.

MS (ESI): m/z 327.0 [M+H]$^+$. NMR: $^1$HNMR (400 MHz, CDCl3) δ: 8.11 (d, J=8.0 Hz, 2H), 7.98 (m, 1H), 7.86 (m, 1H), 7.59 (t, J=8.0 Hz, 7.6 Hz, 1H), 7.33 (d, J=8.0 Hz, 2H), 4.85 (s, 2H), 2.57 (d, J=6.8 Hz, 2H), 1.93 (m, 1H), 0.93 (d, J=6.8 Hz, 6H).

(2) At room temperature, 2-fluoro-4-[5-(4-isobutylphenyl)-1,2,4-oxadiazol-3-yl]-benzyl alcohol (1-5, 1.4 Kg, 4.30 mol) was dissolved in ethyl acetate (14 L), and then active manganese dioxide (2.1 Kg, 24.15 mol) was added in. The reaction liquid was heated to reflux and reacted for 3 hours, cooled to room temperature and filtered. A light yellow filtrate was collected, dried with anhydrous sodium sulfate and concentrated under reduced pressure to obtain 2-fluoro-4-[5-(4-isobutylphenyl)-1,2,4-oxadiazol-3-yl]-benzaldehyde which was a white solid product (1-6, 1.38 kg, 99.0% yield). The purity detected by LCMS was 93.94%.

MS (ESI): m/z 325.0 [M+H]$^+$. NMR: $^1$HNMR (400 MHz, CDCl3) δ: 10.42 (s, 1H), 8.12~7.99 (m, 5H), 7.34 (d, J=7.2 Hz, 2H), 2.58 (d, J=6.4 Hz, 2H), 1.93 (m, 1H), 0.93 (d, J=6.4 Hz, 6H).

(3) At room temperature, 2-fluoro-4-[5-(4-isobutylphenyl)-1,2,4-oxadiazol-3-yl]-benzaldehyde (1-6, 0.6 kg, 1.85 mol), azetidine-3-carboxylic acid (1-7, 0.195 kg, 1.93 mol) and glacial acetic acid (0.360 L, 6.3 mol) were added into methanol (16 L) and stirred for 2 hours at 20° C. NaBH3CN (0.115 kg, 1.85 mol) was dissolved in methanol (2 L), and then the solution of NaBH3CN in methanol was added dropwise into the reaction system within 1 hour. The dropping temperature was controlled at 15-20° C. The reaction liquid was stirred for 16 hours at 20° C. after dropping and filtered. The filter cake was washed with 3 L methanol and then dried to obtain 1-{2-fluoro-4-[5-(4-isobutylphenyl)-1,2,4-oxadiazol-3-yl]-benzyl}-3-azetidine carboxylic acid which was a white solid product (compound 2, 0.7 kg, 92.6% yield). The purity detected by LCMS was 97.6%.

MS (ESI): m/z 410.2 [M+H]$^+$. NMR: $^1$HNMR (400 MHz, CDCl3) δ: 8.13 (d, J=8.4 Hz, 2H), 8.05 (m, 1H), 7.97 (m, 1H), 7.68 (t, J=8.0 Hz, 7.6 Hz, 1H), 7.42 (d, J=8.4 Hz, 2H), 4.40 (s, 2H), 4.15 (m, 4H), 3.41 (m, 1H), 2.61 (d, J=7.2 Hz, 2H), 1.95 (m, 1H), 0.94 (d, J=7.2 Hz, 6H).

Example 17

Synthesis Method of the Present Invention (1) At room temperature, 4-isobutyl benzoicacid (1-4, 0.148 Kg, 0.83 mol) was dissolved in N,N-dimethylformamide (1.7 L), and then 1-hydroxybenzotrizole (0.11 Kg, 0.83 mol) and 1-(3-dimethylaminopropyl)-3-ethylcarbodiimide hydrochloride (0.16 Kg, 0.83 mol) were added in. The reaction liquid was heated to 30° C. and stirred for 30 min, then 3-fluoro-N'-hydroxy-4-hydroxymethyl benzamidine (1-3, 0.153 Kg, 0.83 mol) was added to the reaction liquid. The reaction liquid was heated to 140° C. and reacted for 2 hours, cooled down to room temperature, and the N,N-dimethylformamide was removed by concentration under reduced pressure. The concentrate was dissolved in ethyl acetate (2.0 L), and washed successively with water (1.5 L×2) and saturated NaHCO3 solution (1.5 L). The organic phase was collected and dried with anhydrous sodium sulfate, and concentrated under reduced pressure to obtain 251 g crude product.

The crude product obtained from above was recrystallized by 1.28 L mixed solvent of methanol and water (a volume ratio of 1:1), crystallized at 20° C., filtered and dried in vacuum to obtain 2-fluoro-4-[5-(4-isobutylphenyl)-1,2,4-oxadiazol-3-yl]-benzyl alcohol which was an almost white solid product (1-5, 158 g, 63% yield). The purity detected by LCMS was 92.1%.

MS (ESI): m/z 327.0 [M+H]$^+$. NMR: $^1$HNMR (400 MHz, CDCl3) δ: 8.11 (d, J=8.0 Hz, 2H), 7.98 (m, 1H), 7.86 (m, 1H), 7.59 (t, J=8.0 Hz, 7.6 Hz, 1H), 7.33 (d, J=8.0 Hz, 2H), 4.85 (s, 2H), 2.57 (d, J=6.8 Hz, 2H), 1.93 (m, 1H), 0.93 (d, J=6.8 Hz, 6H).

(2) At room temperature, 2-fluoro-4-[5-(4-isobutylphenyl)-1,2,4-oxadiazol-3-yl]-benzyl alcohol (1-5, 0.14 Kg, 0.43 mol) was dissolved in ethyl acetate (1.4 L), and then active manganese dioxide (0.19 Kg, 2.15 mol) was added in. The reaction liquid was heated to reflux and reacted for 3 hours, cooled to room temperature and filtered. A light yellow filtrate was collected, dried with anhydrous sodium sulfate and concentrated under reduced pressure to obtain 2-fluoro-4-[5-(4-isobutylphenyl)-1,2,4-oxadiazol-3-yl]-benzaldehyde which was a white solid product (1-6, 138 g, 99.0% yield). The purity detected by LCMS was 98.5%.

MS (ESI): m/z 325.0 [M+H]$^+$. NMR: $^1$HNMR (400 MHz, CDCl3) δ: 10.42 (s, 1H), 8.12~7.99 (m, 5H), 7.34 (d, J=7.2 Hz, 2H), 2.58 (d, J=6.4 Hz, 2H), 1.93 (m, 1H), 0.93 (d, J=6.4 Hz, 6H).

(3) At room temperature, 2-fluoro-4-[5-(4-isobutylphenyl)-1,2,4-oxadiazol-3-yl]-benzaldehyde (1-6, 60 g, 0.185 mol), azetidine-3-carboxylic acid (1-7, 19.5 g, 0.193 mol) and glacial acetic acid (360 mL, 0.63 mol) were added into methanol (1.6 L) and stirred for 2 hours at 20° C. NaBH3CN (5.8 g, 0.09 mol) was dissolved in methanol (200 mL), and then the solution of NaBH3CN in methanol was added dropwise into the reaction system within 1 hour. The dropping temperature was controlled at 15-20° C. The reaction liquid was stirred for 16 hours at 20° C. after dropping and filtered. The filter cake was washed with 300 mL methanol and then dried to obtain 1-{2-fluoro-4-[5-(4-isobutylphenyl)-1,2,4-oxadiazol-3-yl]-benzyl}-3-azetidine carboxylic acid which was a white solid product (compound 2, 62 g, 81.9% yield). The purity detected by LCMS was 94.6%.

MS (ESI): m/z 410.2 [M+H]$^+$. NMR: $^1$HNMR (400 MHz, CDCl3) δ: 8.13 (d, J=8.4 Hz, 2H), 8.05 (m, 1H), 7.97 (m, 1H), 7.68 (t, J=8.0 Hz, 7.6 Hz, 1H), 7.42 (d, J=8.4 Hz, 2H), 4.40 (s, 2H), 4.15 (m, 4H), 3.41 (m, 1H), 2.61 (d, J=7.2 Hz, 2H), 1.95 (m, 1H), 0.94 (d, J=7.2 Hz, 6H).

Example 18

Synthesis Method of the Present Invention (1) At room temperature, 4-isobutyl benzoicacid (1-4, 0.148 Kg, 0.83 mol) was dissolved in N,N-dimethylformamide (1.7 L), and then 1-hydroxybenzotrizole (0.11 Kg, 0.83 mol) and 1-(3-dimethylaminopropyl)-3-ethylcarbodiimide hydrochloride (0.16 Kg, 0.83 mol) were added in. The reaction liquid was heated to 30° C. and stirred for 30 min, then 3-fluoro-N'-hydroxy-4-hydroxymethyl benzamidine (1-3, 0.153 Kg, 0.83 mol) was added to the reaction liquid. The reaction liquid was heated to 140° C. and reacted for 2 hours, cooled down to room temperature, and the N,N-dimethylformamide was removed by concentration under reduced pressure. The concentrate was dissolved in ethyl acetate (2.0 L), and washed successively with water (1.5 L×2) and saturated NaHCO3 solution (1.5 L). The organic phase was collected and dried with anhydrous sodium sulfate, and concentrated under reduced pressure to obtain 260 g crude product.

The crude product obtained from above was recrystallized by 1.30 L mixed solvent of methanol and water (a volume ratio of 1:3), crystallized at 20° C., filtered and dried in vacuum to obtain 2-fluoro-4-[5-(4-isobutylphenyl)-1,2,4-oxadiazol-3-yl]-benzyl alcohol which was an almost white solid product (1-5, 196 g, 76% yield). The purity detected by LCMS was 88.7%.

MS (ESI): m/z 327.0 [M+H]$^+$. NMR: $^1$HNMR (400 MHz, CDCl3) δ: 8.11 (d, J=8.0 Hz, 2H), 7.98 (m, 1H), 7.86 (m, 1H), 7.59 (t, J=8.0 Hz, 7.6 Hz, 1H), 7.33 (d, J=8.0 Hz, 2H), 4.85 (s, 2H), 2.57 (d, J=6.8 Hz, 2H), 1.93 (m, 1H), 0.93 (d, J=6.8 Hz, 6H).

(2) At room temperature, 2-fluoro-4-[5-(4-isobutylphenyl)-1,2,4-oxadiazol-3-yl]-benzyl alcohol (1-5, 0.14 Kg, 0.43 mol) was dissolved in ethyl acetate (1.4 L), and then active manganese dioxide (0.21 Kg, 2.42 mol) was added in. The reaction liquid was heated to reflux and reacted for 3 hours, cooled to room temperature and filtered. A light yellow filtrate was collected, dried with anhydrous sodium sulfate and concentrated under reduced pressure to obtain 2-fluoro-4-[5-(4-isobutylphenyl)-1,2,4-oxadiazol-3-yl]-benzaldehyde which was a white solid product (1-6, 139 g, 99.0% yield). The purity detected by LCMS was 97.7%.

MS (ESI): m/z 325.0 [M+H]$^+$. NMR: $^1$HNMR (400 MHz, CDCl3) δ: 10.42 (s, 1H), 8.12~7.99 (m, 5H), 7.34 (d, J=7.2 Hz, 2H), 2.58 (d, J=6.4 Hz, 2H), 1.93 (m, 1H), 0.93 (d, J=6.4 Hz, 6H).

(3) At room temperature, 2-fluoro-4-[5-(4-isobutylphenyl)-1,2,4-oxadiazol-3-yl]-benzaldehyde (1-6, 60 g, 0.185 mol), azetidine-3-carboxylic acid (1-7, 19.5 g, 0.193 mol) and glacial acetic acid (360 mL, 0.63 mol) were added into methanol (1.6 L) and stirred for 2 hours at 20° C. NaBH3CN (23.0 g, 0.37 mol) was dissolved in methanol (200 mL), and then the solution of NaBH3CN in methanol was added dropwise into the reaction system within 1 hour. The dropping temperature was controlled at 15-20° C. The reaction liquid was stirred for 16 hours at 20° C. after dropping and filtered. The filter cake was washed with 300 mL methanol and then dried to obtain 1-{2-fluoro-4-[5-(4-isobutylphenyl)-1,2,4-oxadiazol-3-yl]-benzyl}-3-azetidine carboxylic acid which was a white solid product (compound 2, 60 g, 79% yield). The purity detected by LCMS was 94.2%.

MS (ESI): m/z 410.2 [M+H]$^+$. NMR: $^1$HNMR (400 MHz, CDCl3) δ: 8.13 (d, J=8.4 Hz, 2H), 8.05 (m, 1H), 7.97 (m, 1H), 7.68 (t, J=8.0 Hz, 7.6 Hz, 1H), 7.42 (d, J=8.4 Hz, 2H), 4.40 (s, 2H), 4.15 (m, 4H), 3.41 (m, 1H), 2.61 (d, J=7.2 Hz, 2H), 1.95 (m, 1H), 0.94 (d, J=7.2 Hz, 6H).

Example 19

Synthesis Method of the Present Invention (1) At room temperature, 4-isobutyl benzoicacid (1-4, 0.148 Kg, 0.83 mol) was dissolved in N,N-dimethylformamide (1.7 L), and then 1-hydroxybenzotrizole (0.11 Kg, 0.83 mol) and 1-(3-dimethylaminopropyl)-3-ethylcarbodiimide hydrochloride (0.16 Kg, 0.83 mol) were added in. The reaction liquid was heated to 30° C. and stirred for 30 min, then 3-fluoro-N'-hydroxy-4-hydroxymethyl benzamidine (1-3, 0.153 Kg, 0.83 mol) was added to the reaction liquid. The reaction liquid was heated to 140° C. and reacted for 2 hours, cooled down to room temperature, and the N,N-dimethylformamide was removed by concentration under reduced pressure. The concentrate was dissolved in ethyl acetate (2.0 L), and washed successively with water (1.5 L×2) and saturated NaHCO3 solution (1.5 L). The organic phase was collected and dried with anhydrous sodium sulfate, and concentrated under reduced pressure to obtain 250 g crude product.

The crude product obtained from above was recrystallized by 1.25 L mixed solvent of methanol and water (a volume ratio of 2:1), crystallized at 20° C., filtered and dried in vacuum to obtain 2-fluoro-4-[5-(4-isobutylphenyl)-1,2,4-oxadiazol-3-yl]-benzyl alcohol which was an almost white solid product (1-5, 169 g, 68% yield). The purity detected by LCMS was 93.9%.

MS (ESI): m/z 327.0 [M+H]$^+$. NMR: $^1$HNMR (400 MHz, CDCl3) δ: 8.11 (d, J=8.0 Hz, 2H), 7.98 (m, 1H), 7.86 (m, 1H), 7.59 (t, J=8.0 Hz, 7.6 Hz, 1H), 7.33 (d, J=8.0 Hz, 2H), 4.85 (s, 2H), 2.57 (d, J=6.8 Hz, 2H), 1.93 (m, 1H), 0.93 (d, J=6.8 Hz, 6H).

(2) At room temperature, 2-fluoro-4-[5-(4-isobutylphenyl)-1,2,4-oxadiazol-3-yl]-benzyl alcohol (1-5, 0.14 Kg, 0.43 mol) was dissolved in ethyl acetate (1.414, and then active manganese dioxide (0.37 Kg, 4.3 mol) was added in. The reaction liquid was heated to reflux and reacted for 3 hours, cooled to room temperature and filtered. A light yellow filtrate was collected, dried with anhydrous sodium sulfate and concentrated under reduced pressure to obtain 2-fluoro-4-[5-(4-isobutylphenyl)-1,2,4-oxadiazol-3-yl]-benzaldehyde which was a white solid product (1-6, 139 g, 99.0% yield). The purity detected by LCMS was 99.2%.

MS (ESI): m/z 325.0 [M+H]$^+$. NMR: $^1$HNMR (400 MHz, CDCl3) δ: 10.42 (s, 1H), 8.12~7.99 (m, 5H), 7.34 (d, J=7.2 Hz, 2H), 2.58 (d, J=6.4 Hz, 2H), 1.93 (m, 1H), 0.93 (d, J=6.4 Hz, 6H).

(3) At room temperature, 2-fluoro-4-[5-(4-isobutylphenyl)-1,2,4-oxadiazol-3-yl]-benzaldehyde (1-6, 60 g, 0.185 mol), azetidine-3-carboxylic acid (1-7, 19.5 g, 0.193 mol) and glacial acetic acid (360 mL, 0.63 mol) were added into methanol (1.6 L) and stirred for 2 hours at 20° C. NaBH3CN (69.0 g, 1.11 mol) was dissolved in methanol (200 mL), and then the solution of NaBH3CN in methanol was added dropwise into the reaction system within 1 hour. The dropping temperature was controlled at 15-20° C. The reaction liquid was stirred for 16 hours at 20° C. after dropping and filtered. The filter cake was washed with 300 mL methanol and then dried to obtain 1-{2-fluoro-4-[5-(4-isobutylphenyl)-1,2,4-oxadiazol-3-yl]-benzyl}-3-azetidine carboxylic acid which was a white solid product (compound 2, 2, 54 g, 71.2% yield). The purity detected by LCMS was 94.4%.

MS (ESI): m/z 410.2 [M+H]$^+$. NMR: $^1$HNMR (400 MHz, CDCl3) δ: 8.13 (d, J=8.4 Hz, 2H), 8.05 (m, 1H), 7.97 (m, 1H), 7.68 (t, J=8.0 Hz, 7.6 Hz, 1H), 7.42 (d, J=8.4 Hz, 2H), 4.40 (s, 2H), 4.15 (m, 4H), 3.41 (m, 1H), 2.61 (d, J=7.2 Hz, 2H), 1.95 (m, 1H), 0.94 (d, J=7.2 Hz, 6H).

Example 20

Synthesis Method of the Present Invention (1) At room temperature, 4-isobutyl benzoicacid (14, 0.148 Kg, 0.83 mol) was dissolved in N,N-dimethylformamide (1.7 L), and then 1-hydroxybenzotrizole (0.11 Kg, 0.83 mol) and 1-(3-dimethylaminopropyl)-3-ethylcarbodiimide hydrochloride (0.16 Kg, 0.83 mol) were added in. The reaction liquid was heated to 30° C. and stirred for 30 min, then 3-fluoro-N'-hydroxy-4-hydroxymethyl benzamidine (1-3, 0.153 Kg, 0.83 mol) was added to the reaction liquid. The reaction liquid was heated to 140° C. and reacted for 2 hours, cooled down to room temperature, and the N,N-dimethylformamide was removed by concentration under reduced pressure. The concentrate was dissolved in ethyl acetate (2.0 L), and washed successively with water (1.5 L×2) and saturated NaHCO3 solution (1.5 L). The organic phase was collected and dried with anhydrous sodium sulfate, and concentrated under reduced pressure to obtain 256 g crude product.

The crude product obtained from above was recrystallized by 1.28 L mixed solvent of methanol and water (a volume ratio of 1:2), crystallized at 20° C., filtered and dried in vacuum to obtain 2-fluoro-4-[5-(4-isobutylphenyl)-1,2,4-oxadiazol-3-yl]-benzyl alcohol which was an almost white solid product (1-5, 190 g, 74% yield). The purity detected by LCMS was 92.6%.

MS (ESI): m/z 327.0 [M+H]$^+$. NMR: $^1$HNMR (400 MHz, CDCl3) δ: 8.11 (d, J=8.0 Hz, 2H), 7.98 (m, 1H), 7.86 (m, 1H), 7.59 (t, J=8.0 Hz, 7.6 Hz, 1H), 7.33 (d, J=8.0 Hz, 2H), 4.85 (s, 2H), 2.57 (d, J=6.8 Hz, 2H), 1.93 (m, 1H), 0.93 (d, J=6.8 Hz, 6H).

(2) At room temperature, 2-fluoro-4-[5-(4-isobutylphenyl)-1,2,4-oxadiazol-3-yl]-benzyl alcohol (1-5, 0.14 Kg, 0.43 mol) was dissolved in ethyl acetate (1.4 L), and then active manganese dioxide (0.15 Kg, 1.72 mol) was added in. The reaction liquid was heated to reflux and reacted for 3 hours, cooled to room temperature and filtered. A light yellow filtrate was collected, dried with anhydrous sodium sulfate and concentrated under reduced pressure to obtain 2-fluoro-4-[5-(4-isobutylphenyl)-1,2,4-oxadiazol-3-yl]-benzaldehyde which was a white solid product (1-6, 139 g, 99.0% yield). The purity detected by LCMS was 96.9%.

MS (ESI): m/z 325.0 [M+H]$^+$. NMR: $^1$HNMR (400 MHz, CDCl3) δ: 10.42 (s, 1H), 8.12~7.99 (m, 5H), 7.34 (d, J=7.2 Hz, 2H), 2.58 (d, J=6.4 Hz, 2H), 1.93 (m, 1H), 0.93 (d, J=6.4 Hz, 6H).

(3) At room temperature, 2-fluoro-4-[5-(4-isobutylphenyl)-1,2,4-oxadiazol-3-yl]-benzaldehyde (1-6, 60 g, 0.185 mol), azetidine-3-carboxylic acid (1-7, 19.5 g, 0.193 mol) and glacial acetic acid (360 mL, 0.63 mol) were added into methanol (1.6 L) and stirred for 2 hours at 20° C. NaBH3CN (11.5 g, 0.185 mol) was dissolved in methanol (200 mL), and then the solution of NaBH3CN in methanol was added dropwise into the reaction system within 1 hour. The dropping temperature was controlled at 15-20° C. The reaction liquid was stirred for 16 hours at 20° C. after dropping and filtered. The filter cake was washed with 300 mL methanol and then dried to obtain 1-{2-fluoro-4-[5-(4-isobutylphenyl)-1,2,4-oxadiazol-3-yl]-benzyl}-3-azetidine carboxylic acid which was a white solid product (compound 2, 64 g, 84.4% yield). The purity detected by LCMS was 95.5%.

MS (ESI): m/z 410.2 [M+H]$^+$. NMR: $^1$HNMR (400 MHz, CDCl3) δ: 8.13 (d, J=8.4 Hz, 2H), 8.05 (m, 1H), 7.97 (m, 1H), 7.68 (t, J=8.0 Hz, 7.6 Hz, 1H), 7.42 (d, J=8.4 Hz, 2H), 4.40 (s, 2H), 4.15 (m, 4H), 3.41 (m, 1H), 2.61 (d, J=7.2 Hz, 2H), 1.95 (m, 1H), 0.94 (d, J=7.2 Hz, 6H).

Example 21

Synthesis Method of the Present Invention (1) At room temperature, 4-isobutyl benzoicacid (14 0.148 Kg, 0.83 mol) was dissolved in N,N-dimethylformamide (1.7 L), and then 1-hydroxybenzotrizole (0.11 Kg, 0.83 mol) and 1-(3-dimethylaminopropyl)-3-ethylcarbodiimide hydrochloride (0.16 Kg, 0.83 mol) were added in. The reaction liquid was heated to 30° C. and stirred for 30 min, then 3-fluoro-N-hydroxy-4-hydroxymethyl benzamidine (1-3, 0.153 Kg, 0.83 mol) was added to the reaction liquid. The reaction liquid was heated to 140° C. and reacted for 2 hours, cooled down to room temperature, and the N,N-dimethylformamide was removed by concentration under reduced pressure. The concentrate was dissolved in ethyl acetate (2.0 L), and washed successively with water (1.5 L×2) and saturated NaHCO3 solution (1.5 L) The organic phase was collected and dried with anhydrous sodium sulfate, and concentrated under reduced pressure to obtain 258 g crude product.

The crude product obtained from above was recrystallized by 1.29 L mixed solvent of methanol and water (a volume ratio of 3:1), crystallized at 20° C., filtered and dried in vacuum to obtain 2-fluoro-4-[5-(4-isobutylphenyl)-1,2,4-oxadiazol-3-yl]-benzyl alcohol which was an almost white solid product (1-5, 186 g, 72% yield). The purity detected by LCMS was 93.8%.

MS (ESI): m/z 327.0 [M+H]$^+$. NMR: $^1$HNMR (400 MHz, CDCl3) δ: 8.11 (d, J=8.0 Hz, 2H), 7.98 (m, 1H), 7.86 (m, 1H), 7.59 (t, J=8.0 Hz, 7.6 Hz, 1H), 7.33 (d, J=8.0 Hz, 2H), 4.85 (s, 2H), 2.57 (d, J=6.8 Hz, 2H), 1.93 (m, 1H), 0.93 (d, J=6.8 Hz, 6H).

(2) At room temperature, 2-fluoro-4-[5-(4-isobutylphenyl)-1,2,4-oxadiazol-3-yl]-benzyl alcohol (1-5, 0.14 Kg, 0.43 mol) was dissolved in ethyl acetate (2.8 L), and then active manganese dioxide (0.21 Kg, 2.42 mol) was added in. The reaction liquid was heated to reflux and reacted for 3 hours, cooled to room temperature and filtered. A light yellow filtrate was collected, dried with anhydrous sodium sulfate and concentrated under reduced pressure to obtain 2-fluoro-4-[5-(4-isobutylphenyl)-1,2,4-oxadiazol-3-yl]-benzaldehyde which was a white solid product (1-6, 138 g, 99% yield). The purity detected by LCMS was 98.8%.

MS (ESI): m/z 325.0 [M+H]+, NMR: $^1$HNMR (400 MHz, CDCl3) δ: 10.42 (s, 1H), 8.12~7.99 (m, 5H), 7.34 (d, J=7.2 Hz, 2H), 2.58 (d, J=6.4 Hz, 2H), 1.93 (m, 1H), 0.93 (d, J=6.4 Hz, 6H).

(3) At room temperature, 2-fluoro-4-[5-(4-isobutylphenyl)-1,2,4-oxadiazol-3-yl]-benzaldehyde (1-6, 60 g, 0.185 mol), azetidine-3-carboxylic acid (1-7, 19.5 g, 0.193 mol) and glacial acetic acid (360 mL, 0.63 mol) were added into methanol (1.6 L) and stirred for 2 hours at 20° C. NaBH3CN (11.5 g, 0.185 mol) was dissolved in methanol (200 mL), and then the solution of NaBH3CN in methanol was added dropwise into the reaction system within 1 hour. The dropping temperature was controlled at 15-20° C. The reaction liquid was stirred for 16 hours at 20° C. after dropping and filtered. The filter cake was washed with 300 mL methanol and then dried to obtain 1-{2-fluoro-4-[5-(4-isobutylphenyl)-1,2,4-oxadiazol-3-yl]-benzyl}-3-azetidine carboxylic acid which was a white solid product (compound 2, 64 g, 84.5% yield). The purity detected by LCMS was 96.9%.

MS (ESI): m/z 410.2 [M+H]+. NMR: 1HNMR (400 MHz, CDCl3) δ: 8.13 (d, J=8.4 Hz, 2H), 8.05 (m, 1H), 7.97 (m, 1H), 7.68 (t, J=8.0 Hz, 7.6 Hz, 1H), 7.42 (d, J=8.4 Hz, 2H), 4.40 (s, 2H), 4.15 (m, 4H), 3.41 (m, 1H), 2.61 (d, J=7.2 Hz, 2H), 1.95 (m, 1H), 0.94 (d, J=7.2 Hz, 6H).

The above description for the embodiments of the present invention is not intended to limit the present invention, and those skilled in the art can make various changes and variations according to the present invention, which are within the protection scope of the present invention without departing from the spirit of the same.

What is claimed is:

1. A compound as shown in Formula I:

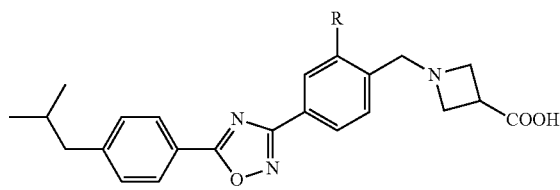

Formula I wherein, R is halogen.

2. The compound according to claim 1, wherein R is F, Cl or Br.

3. A pharmaceutical composition comprising the compound according to claim 1 and optionally a pharmaceutically acceptable carrier.

4. The pharmaceutical composition according to claim 3, wherein the pharmaceutical composition is in a form of tablet, suppository, dispersible tablet, enteric-coated tablet, chewable tablet, orally disintegrating tablet, capsule, sugar-coated agent, granule, dry powder, oral solution, small needle for injection, lyophilized powder or large volume parenteral solution for injection.

5. A method for treating disease or condition mediated by S1P1, comprising administering to a subject a therapeutically effective amount of the compound according to claim 1.

6. The method according to claim 5, wherein said subject is a mammalian.

7. The method according to claim 5, wherein said disease or condition is selected from the group consisting of rheumatoid arthritis, multiple sclerosis, inflammatory enteritis, autoimmune disease, chronic inflammatory disease, asthma, inflammatory neuropathies, arthritis, transplantation, Crohn's disease, ulcerativecolitis, lupus erythematosus, psoriasis, ischemia-reperfusion injury, solid tumor, disease associated with angiogenesis, disease of blood vessel, pain, acute viral disease, inflammatory bowel disease, insulin and non-insulin dependent diabetes mellitus, and other related immune diseases.

8. A synthesis method of 1-{2-fluoro-4-[5-(4-isobutylphenyl)-1,2,4-oxadiazol-3-yl]-benzyl}-3-azetidine carboxylic acid, comprising the following steps:

(1) reacting 3-fluoro-N'-hydroxy-4-hydroxymethyl benzamidine as shown in formula 1-3 with 4-isobutylbenzoicacid as shown in formula 1-4 in the presence of condensation agents 1-(3-dimethylaminopropyl)-3-ethylcarbodiimide hydrochloride and 1-hydroxybenzotrizole to generate 2-fluoro-4-[5-(4-isobutylphenyl)-1,2,4-oxadiazol-3-yl]-benzyl alcohol as shown in formula 1-5:

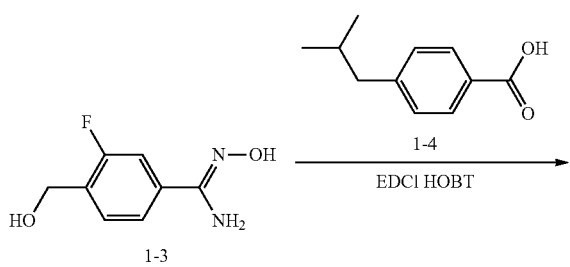

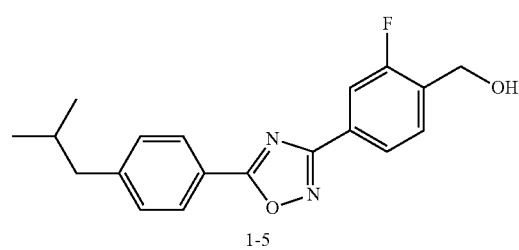

(2) reacting 2-fluoro-4-[5-(4-isobutylphenyl)-1,2,4-oxadiazol-3-yl]benzyl alcohol as shown in formula 1-5obtained in step (1) with manganese dioxide to generate 2-fluoro-4-[5-(4-isobutylphenyl)-1,2,4-oxadiazol-3-yl]benzaldehyde as shown in formula 1-6:

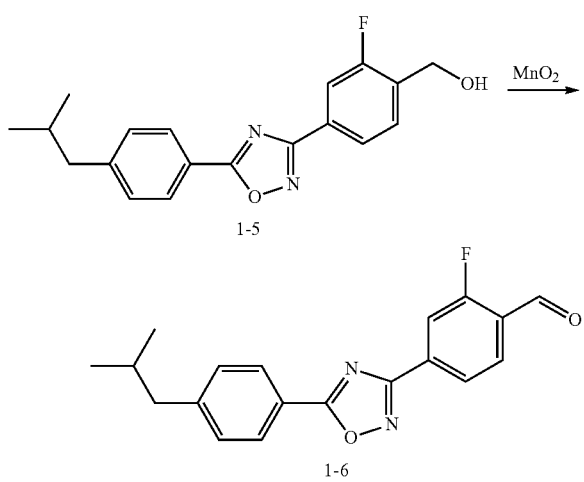

(3) reacting 2-fluoro-4-[5-(-4-isobutylphenyl)-1,2,4-oxadiazol-3-yl]-benzaldehyde as shown in formula 1-6 obtained in step (2) with azetidine-3-carboxylic acid as shown in formula 1-7 by using acetic acid as catalyst and sodium cyanoborohydride as reducing agent to generate the compound as shown in formula IB:

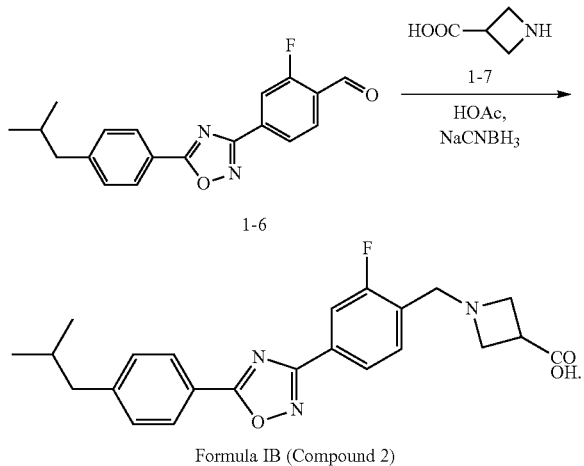

Formula IB (Compound 2)

9. The synthesis method according to claim 8, wherein step (1) also comprises a step of purifying the obtained crude product after the generation of 2-fluoro-4-[5-(4-isobutylphenyl)-1,2,4-oxadiazol-3-yl]-benzyl alcohol as shown in formula 1-5; and wherein, the purification is conducted through column chromatography or crystallization.

10. The synthesis method according to claim 9, wherein when conducting purification through crystallization, a crystallization solvent utilized is a mixture of methanol and water.

11. The synthesis method according to claim 8, wherein the reaction of step (1) is carried out in a reaction solvent which is one or more selected from acetonitrile, N-methylpyrrolidone and N,N-dimethylformamide; the reaction is conducted at a temperature of 80-140° C.; and a mole ratio of 3-fluoro-N'-hydroxy-4-hydroxymethyl benzamidine as shown in formula 1-3 and 4-isobutylbenzoicacid as shown in formula 1-4 is 1: 1-2.0.

12. The synthesis method according to claim 8, wherein in step (1), a reaction solvent is N,N-dimethylformamide; the reaction is conducted at a temperature of 130-140° C.; and a mole ratio of 3-fluoro-N'-hydroxy-4-hydroxymethyl benzamidine as shown in formula 1-3 to 4-isobutylbenzoicacid as shown in formula 1-4 is 1: 1-1.5.

13. The synthesis method according to claim 8, wherein the reaction of step (2) is carried out in a reaction solvent which is one or more selected from toluene, tetrahydrofuran and ethyl acetate; a ratio of 2-fluoro-4-[5-(4-isobutylphenyl)-1,2,4-oxadiazol-3-yl]-benzyl alcohol as shown in formula 1-5 (in g, by weight) to the reaction solvent (in ml, by volume) is 1: 10-30; the reaction is conducted at a temperature of 40-70° C.; and a mole ratio of 2-fluoro-4-[5-(4-isobutylphenyl)-1,2,4-oxadiazol-3-yl]-benzyl alcohol as shown in formula 1-5 to manganese dioxide is 1: 4-10.

14. The synthesis method according to claim 8, wherein in step (2), a reaction solvent is ethyl acetate;

a ratio of 2-fluoro-4-[5-(4-isobutylphenyl)-1,2,4-oxadiazol-3-yl]-benzyl alcohol as shown in formula 1-5 (in g, by weight) to the reaction solvent (in ml, by volume) is 1: 10; and a reaction temperature is 60-70° C.

15. The synthesis method according to claim 8, wherein the reaction of step (3) is carried out in a reaction solvent which is selected from tetrahydrofuran and/or methanol; a mole ratio of 2-fluoro-4-[5-(4-isobutylphenyl)-1,2,4-oxadiazol-3-yl]-benzaldehyde as shown in formula 1-6 to azetidine-3-carboxylic acid as shown in formula 1-7 is 1: 1-1.2; a mole ratio of 2-fluoro-4-[5-(4-isobutylphenyl)-1,2,4-oxadiazol-3-yl]-benzaldehyde as shown in formula 1-6 to sodium cyanoborohydride is 1: 0.5-6; the reaction is conducted at a temperature of 0-30° C. for a reaction period of 1-16 hours.

16. The synthesis method according to claim 8, wherein in step (3), a reaction solvent is methanol;

a reaction temperature is 10-20° C.; and a reaction period is 4-16 hours.

17. A pharmaceutical composition comprising the compound according to claim 2 and optionally a pharmaceutically acceptable carrier.

18. The method according to claim 7, wherein said disease or condition is selected from the group consisting of multiple sclerosis, rheumatoid arthritis, inflammatory enteritis and psoriasis.

19. The method according to claim 10, wherein the crystallization solvent is a mixture of methanol and water in a ratio of 3: 1 by volume, and the ratio of the crude product (in g, by weight) to the crystallization solvent (in ml, by volume) is 1: 3-20.

20. The method according to claim 19, wherein the ratio of the crude product (in g, by weight) to the crystallization solvent (in ml, by volume) is 1: 5.

21. The method according to claim 10, wherein the crystallization is carried out at 20° C.

22. The method according to claim 14, wherein a mole ratio of 2-fluoro-4-[5-(4-isobutylphenyl)-1,2,4-oxadiazol-3-yl]-benzyl alcohol as shown in formula 1-5 to manganese dioxide is 1: 5-6.

23. The method according to claim 16, wherein a mole ratio of 2-fluoro-4-[5-(4-isobutylphenyl)-1,2,4-oxadiazol-3-yl]-benzaldehyde as shown in formula 1-6 to azetidine-3-carboxylic acid as shown in formula 1-7 is 1: 1-1.1.

24. The method according to claim 16, wherein the sodium cyanoborohydride is dissolved in methanol and dropped into the reaction at a temperature of 15-20° C.

25. The method according to claim 16, wherein a mole ratio of 2-fluoro-4-[5-(4-isobutylphenyl)-1,2,4-oxadiazol-3-yl]-benzaldehyde as shown in formula 1-6 to sodium cyanoborohydride is 1: 1.

* * * * *